United States Patent [19]
Delespesse

[11] Patent Number: 5,843,676
[45] Date of Patent: Dec. 1, 1998

[54] PURIFIED IMMUNOGLOBULIN-RELATED FACTOR, NOVEL MONOCLONAL ANTIBODIES, HYBRIDOMA CELL LINES, PROCESSES AND APPLICATIONS

[75] Inventor: Guy Delespesse, Winnipeg Manitoba, Canada

[73] Assignee: Ciba-Geigy Corporation, Tarrytown, N.Y.

[21] Appl. No.: 649,922

[22] Filed: May 16, 1996

Related U.S. Application Data

[63] Continuation of Ser. No. 170,643, Dec. 20, 1993, abandoned, which is a continuation of Ser. No. 420,848, Oct. 13, 1989, abandoned, which is a division of Ser. No. 870,573, Jun. 4, 1986, Pat. No. 4,946,788.

[30] Foreign Application Priority Data

| Jun. 11, 1985 | [GB] | United Kingdom | 8514732 |
| Oct. 21, 1985 | [GB] | United Kingdom | 8525882 |
| Nov. 11, 1985 | [GB] | United Kingdom | 8527765 |

[51] Int. Cl.⁶ ............ G01N 33/53; C07K 16/00; C07K 1/00; A23J 1/00

[52] U.S. Cl. ............ 435/7.1; 435/7.8; 435/7.92; 435/219; 435/240.27; 436/513; 436/518; 436/541; 436/823; 436/524; 530/387.1; 530/350; 530/412; 530/413; 530/862

[58] Field of Search ............ 435/7.1, 7.8, 219, 435/183, 240.27, 7.92; 436/501, 506, 513, 518, 541, 823, 824; 530/387.1, 396, 350, 399, 412, 413, 827, 830, 832, 862

[56] References Cited

U.S. PATENT DOCUMENTS 4,866,037  9/1989  Delespesse ............ 530/350

FOREIGN PATENT DOCUMENTS

| 0155192 | of 0000 | European Pat. Off. . |
| 0190099 | 7/1986 | European Pat. Off. . |
| 0254249 | 7/1989 | European Pat. Off. . |
| 8100813 | 4/1981 | WIPO . |
| WO86/06407 | 4/1986 | WIPO . |

OTHER PUBLICATIONS

P.P. Chen et al. J Immunol. Methods 58, 59 (1983).
P. Jardieu et al, J. Immunol. 135 2727 (Oct. 1985).
K. Ishizaka et al., Int. Archs. Applic. Immun. 77 13 (1985).
M. Sarfati et al. Immunol. 53, 197 (1984).
M. Sarfati et al. Immunol. 53, 207 (1984).
M. Sarfari et al, Immunol. 53 783 (1984).
T. F. Huff & K. Ishizaka, Proc. Math. Acad. Sci. USA 81, 1514 (1984).
C.L. Martens et al., Proc. Math. Acad. Sci. U.S.A. 82, 2460 (1985).
T. F. Huff et al, J. Immumol. 132, 406(1984).
K.W. Moore et al., J. Immunol. 136, 4283 (Jun. 1, 1986).

*Primary Examiner*—Bradley L. Sisson
*Attorney, Agent, or Firm*—Henry P. Nowak; James Scott Elmer

[57] ABSTRACT

The invention relates to novel purified human immunoglobulin E binding factors (IgE-BFs), its individual optionally glycosylated proteins, and fragments thereof, processes for the purification of IgE-BFs, novel monoclonal antibodies to lymphocyte cellular receptors for IgE ($Fc_\epsilon R$) crossreacting with IgE-BFs, derivatives thereof, processes for the preparation of these antibodies and their derivatives, hybridoma cell lines that produce these antibodies, processes for the preparation of said hybridoma cell lines, the use of the monoclonal antibodies and their derivatives for the qualitative and quantitative determination of IgE-BFs, test kits containing the monoclonal antibodies and/or their derivatives, the use of the monoclonal antibodies for the purification of IgE-BFs, the use of purified IgE-BFs, its individual optionally glycosylated proteins and/or fragments thereof for the prevention and/or treatment of allergy, and to pharmaceutical preparations containing them. IgE-BFs and monoclonal antibodies reacting with IgE-BF are important for the diagnosis and therapy of allergic diseases.

8 Claims, 6 Drawing Sheets

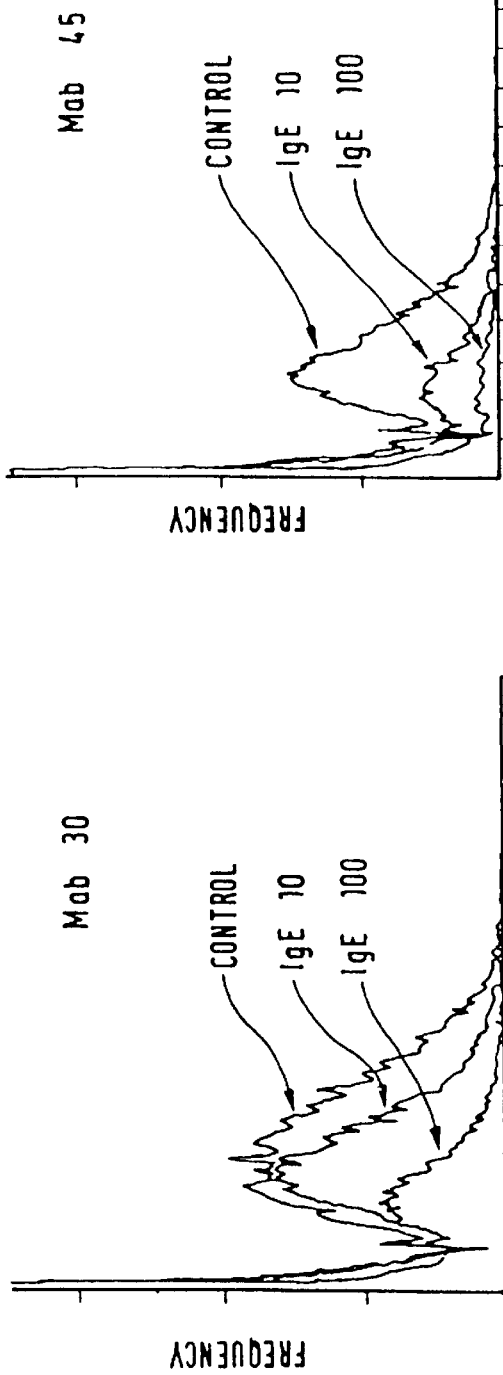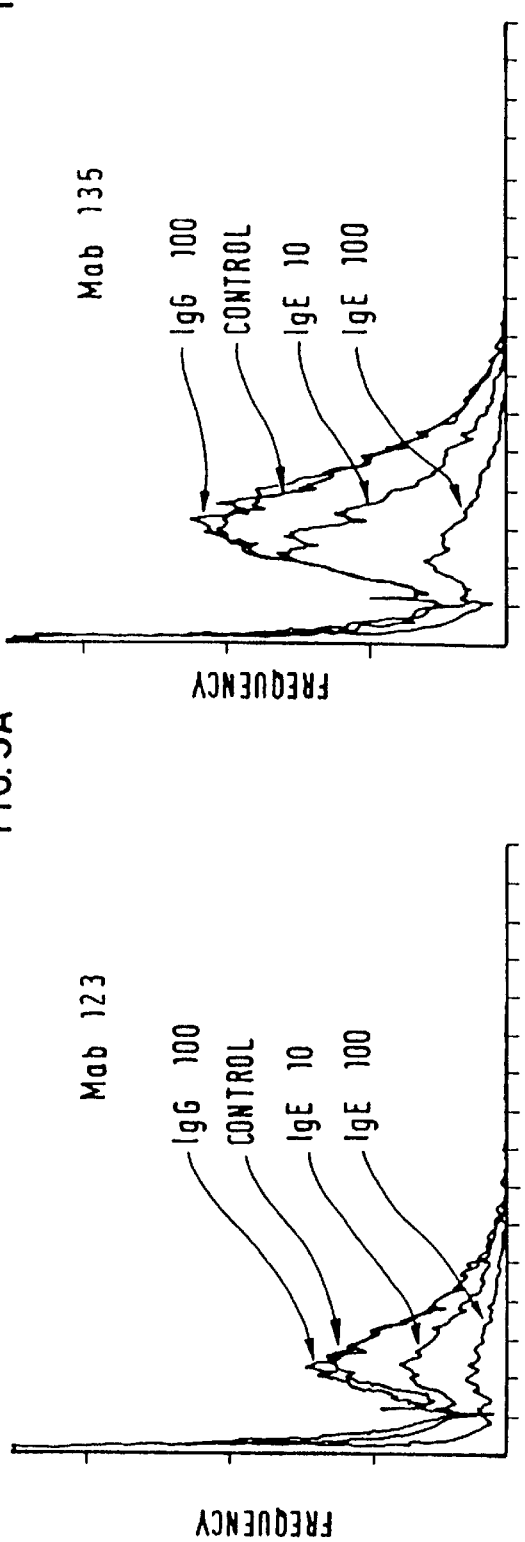

PURIFIED IMMUNOGLOBULIN-RELATED FACTOR, NOVEL MONOCLONAL ANTIBODIES, HYBRIDOMA CELL LINES, PROCESSES AND APPLICATIONS

This application is a continuation of application Ser. No. 08/170,643, filed Dec. 20, 1993, now abandoned which is a continuation of application Ser. No. 07/420,848, filed Oct. 13, 1989, now abandoned, which is a division of application Ser. No. 06/870,573, filed Jun. 4, 1986, patented, U.S. Pat. No. 4,946,788.

The invention relates to novel purified human immunoglobulin E binding factors (IgE-BFs), its individual optionally glycosylated proteins, and fragments thereof, processes for the purification of IgE-BFs, novel monoclonal antibodies to lymphocyte cellular receptors for IgE ($Fc_\epsilon R$) crossreacting with IgE-BFs, derivatives thereof, processes for the preparation of these antibodies and their derivatives, hybridoma cell lines that produce these antibodies, processes for the preparation of said hybridoma cell lines, the use of the monoclonal antibodies and their derivatives for the qualitative and quantitative determination of IgE-BFs, test kits containing the monoclonal antibodies and/or their derivatives, the use of the monoclonal antibodies for the purification of IgE-BFs, the use of purified IgE-BFs, its individual optionally glycosylated proteins and/or fragments thereof for the prevention and/or the treatment of allergic diseases, and to pharmaceutical preparations containing them.

BACKGROUND OF THE INVENTION

Allergic diseases are still a major health problem due to their high incidence (20 to 30% of the population) and to the lack of curative treatment. Usually the therapy is restricted to the use of antihistamines or to more or less effective immunization procedures. The classical antiallergic drugs have certain disadvantages, especially since they cause various side effects in the treated patient. The immunization procedure is limited to one or two allergens whereas most of the patients are sensitive to a large number of allergens. In addition, hyposensitization treatment is neither curative nor protective.

The vast majority of allergic diseases are mediated by immunoglobulin E (IgE) antibodies directed against a myriad of airborne allergens, e.g. pollens, animal danders or house dust mite, etc., food antigens, pharmacological agents, e.g. penicillins, or hyme-noptera venom. The mechanisms regulating the production of IgE have been extensively investigated in laboratory animals [K. Ishizaka, Ann. Rev. Immunol. 2, 159 (1984)]. These studies have clearly indicated the existence of non antigen specific but IgE isotype specific mechanisms controlling the production of IgE in animal models. The effector molecules of these regulatory mechanisms were named IgE-binding factors (IgE-BFs) owing to their affinity for IgE. IgE-BFs may be divided into IgE-suppressive factors (IgE-SFs) and IgE-potentiating factors (IgE-PFs): These molecules differ only by their carbohydrate content. IgE-SFs are not glycosylated or less glycosylated than the corresponding IgE-PFs. The actual production of IgE in animal models is determined by the ratio between these two kinds of IgE-BFs.

The same cells are capable of secreting either IgE-SFs or IgE-PFs depending on the influence of either glycosylation inhibiting or enhancing factors which are secreted by distinct regulatory T lymphocyte subpopulations.

M. Sarfati et al. [Immunology 53, 197, 207, 783 (1984)] have documented the existence of human B cell lines secreting IgE-BFs endowed with the same biological activities as those described in rodents. Other investigators have described the production of IgE-BFs by human T cells [T. F. Huff and K. Ishizaka, Proc. Natl. Acad. Sci. (USA) 81, 1514 (1984)] and rat/mouse T-cell hybridoma [European Patent Application 155 192]. The relationships between IgE-BFs of T cell origin and those of B cell origin are not known. The present invention now provides IgE-BFs from human B cells in highly purified form.

It is already known that breast-feeding may alter the immune reactivity of the newborn. Recent prospective studies further indicated that exclusive breast-feeding protects the high risk infants against allergic disease. Multiple mechanisms are invoked to explain these observations: (i) A reduced exposure to foreign food antigens, (ii) the protection by milk IgA blocking antibodies specific to various alimentary antigens and to other environmental antigens, (iii) the protection against common viral diseases known to trigger the onset of allergic diseases, and finally (iv) the presence in human milk of immunoregulatory factors capable of modulating the immature immune system of the neonate [S. S. Crago and J. Mestecky, Surv. Immunol. Res. 2, 164 (1983)]. The well documented observation on the immunoreactivity of breast-fed newborns might be explained by the presence in human colostrum of specific antibodies or idiotypes, immunoregulatory factors, or regulatory lymphocytes. Hence, it is suggested that breast-feeding may protect newborns by providing them with either IgE-suppressive factors or with other molecules (such as glycosylation inhibiting factor) or cells capable of interfering with the infants lymphocytes involved in the regulation of IgE antibody production [S. A. Roberts and M. W. Turner, Immunology 48, 195 (1983); E. Jarrett and E. Hall, Nature 280, 145 (1979)].

So far IgE-BFs with IgE-SF activity have not been identified in human colostrum, and the isolation thereof is nowhere described. Surprisingly, such IgE-BFs have now been isolated in highly purified form.

IgE plays an important role in the development of allergic diseases. Purified IgE-binding factors are therefore important for the diagnosis and therapy of allergic diseases and immune regulation diseases connected therewith. In particular IgE-BFs with IgE-suppressive activity might be useful in the treatment of allergic diseases, whereas IgE-BFs with IgE-potentiating activity might increase resistance to infections, for example resistance to parasitic infections.

The known assays for the detection of IgE-BFs are based on a rosette inhibition test wherein RPMI 8866 cells from a lymphoblastoid B cell line expressing receptors for IgE (Fce R) are rosetted with IgE-coated bovine erythrocytes. If the latter are first preincubated with IgE-BFs, they are no longer able to bind to RPMI 8866 cells and the proportion of cells forming rosettes is reduced accordingly. This assay is not quantitative, it is technically delicate due to the variability in the coupling of IgE to bovine erythrocytes and it is cumbersome, because rosettes must be examined under the microscope, cell lines must be permanently available, IgE-coated erythrocytes must be prepared regularly, etc., so that only a small number of tests (20–40) can be reasonably performed by one person in one day. Hence, it would be most desirable to dispose of a quantitative, easy to perform assay that could be applied on a large number of samples, e.g. several hundreds per day. Such an assay would not only facilitate the research on the physiopathology of IgE-BFs but it might also be employed to monitor the purification of IgE-BFs from various biological fluids, such as culture supernatants from cell lines secreting IgE-BFs. Furthermore, it could be employed to detect and quantify IgE-BFs in the serum for diagnostic purposes.

The present invention provides a solution to the aforementioned problems through the preparation of monoclonal antibodies to lymphocyte Fc$_\epsilon$R crossreacting with IgE-BFs. At the same time these monoclonal antibodies allow an efficient purification of IgE-BFs by affinity chromatography. The known purification of IgE-BFs by affinity chromatography on IgE-coupled solid phase has been entailed with a low yield compromising further studies on the purified factor due to the low affinity of IgE to IgE-BFs.

OBJECT OF THE INVENTION

A first object of the present invention is to provide IgE binding factors (IgE-BFs) in purified form, its individual optionally glycosylated proteins, and fragments thereof, and a method of their isolation.

A further object of the invention is to provide monoclonal antibodies useful for the qualitative and quantitative determination and for the purification of IgE-BFs.

A third object of the invention is to provide a method for the prevention and/or the treatment of allergy by administering the IgE-BFs, the individual proteins or fragments of the invention, and to provide pharmaceutical compositions comprising them.

DESCRIPTION OF THE INVENTION

The present invention relates to purified human immunoglobulin E binding factor (IgE-BF), its individual optionally glycosylated proteins, and fragments thereof. In a preferred embodiment of the invention, this purified IgE-BF and its constituents are isolated from human B cell supernatants or from human colostrum.

For instance, purified IgE-BFs of the invention are characterized as follows:

(1) They contain only optionally glycosylated proteins of human origin that are recognized and bound by monoclonal antibodies to lymphocyte receptors for IgE (Fc$_\epsilon$R).

(2) They consist of molecules with apparent approximate molecular weight of 25–28 KD (kilo-Dalton, kg/mole) as determined by SDS polyacrylamide gel electrophoresis (SDS-PAGE) and silver staining, and optionally other proteins binding to monoclonal antibodies specific for Fc$_\epsilon$R, e.g. dimers of 45–60 KD and/or partially digested proteins of lower molecular weight, i.e. 10–20 KD.

(3) They reversely bind to IgE, e.g. as determined by their adsorption to and possible recovery from agarose gel bound IgE.

(4) They block the binding of IgE to cells bearing receptors for IgE (Fc$_\epsilon$R$^+$), e.g. as determined by inhibiting the binding of IgE-coated latex particles to RPMI 8866 cells expressing Fc$_\epsilon$R.

(5) They block the binding of IgE to monoclonal antibodies specific to IgE, e.g. as determined with radiolabelled IgE and monoclonal antibodies thereto fixed on microtiter plates.

(6) They are constituents of culture supernatants of human B cells expressing receptors for IgE (Fc$_\epsilon$R$^+$) or of human colostrum.

The individual IgE-BF proteins of the above IgE-BFs are characterized as follows:

(1) They are constituents of an IgE-BF as characterized hereinbefore.

(2) They are homogeneous according to the customary methods of protein analysis, e.g. SDS-PAGE or gel filtration high pressure liquid chromatography.

(3) They are optionally glycosylated.

(4) They have an apparent molecular weight of 25–28 KD as determined by SDS-PAGE.

(5) They have the following approximate range of total amino acid composition: Aspartic acid/asparagine 19–23, glutamic acid/glutamine 25–31, serine 22–26, threonine 8–10, glycine 15–25, alanine 16–20, arginine 10–12, proline 13–16, valine 10–12, methionine 3–5, isoleucine 7–9, leucine 13–17, tryptophan 0, phenylalanine 6–9, cysteine 3–4, lysine 8–10, histidine 4–5, and tyrosine 6–8.

It should be understood that by SDS-PAGE only approximate molecular weights can be determined and that actual molecular weights of the compounds of the invention are in the range of 20–35 KD. Likewise the actual amino acid composition may differ from the range of amino acids given hereinbefore due to uncertainties of the method of total amino acid analysis.

Some of these individual IgE-BF proteins are bound by the monoclonal antibody with the designation 208.25 A.4.3/135, but not bound by the monoclonal antibody with the designation 208.25 D.2/94 to a significant extent, and vice versa.

The individual IgE-BF proteins may be glycosylated or devoid of carbohydrate residues. Typically, a glycosylated IgE-BF protein contains one or more carbohydrate residue, e.g. N-acetylglucosamine or an oligosaccharide containing N-acetylglucosamine N-glycosidically linked to an asparagine residue and/or N-acetylgalactosamine or an oligosaccharide containing N-acetylgalactosamine 0-glycosidically linked to a serine or threonine residue. The oligosaccharides may include sialic acids such as N-acetylneuraminate or N-glycolylneuraminate.

The invention relates also to fragments of IgE-BFs characterized in that:

(1) They are optional constituents of an IgE-BF as characterized hereinbefore.

(2) They are homogeneous according to the customary methods of protein analysis, e.g. SDS-PAGE or gel filtration high pressure liquid chromatography.

(3) They have an apparent molecular weight of 10–20 KD, preferably 14–16 KD, as determined by SDS-PAGE.

(4) They are obtainable by partial enzymatic digestion of the individual IgE-BF proteins characterized hereinbefore.

The invention relates also to a process for the preparation of purified IgE-BF, its individual optionally glycosylated proteins, and fragments thereof, characterized in that a solution containing IgE-BF, for example a culture supernatant of IgE-BF producing cells such as RPMI 8866 cells or a human colostrum preparation, is brought into contact with a carrier material bearing monoclonal antibodies specific to Fc$_\epsilon$R, unbound proteins and other foreign substances are removed, the IgE-BF bound to the antibodies on the carrier is selectively split off and is isolated, and, if desired, the purified IgE-BF is separated into its individual optionally glycosylated proteins and/or fragments thereof.

Cell culture supernatants or cell extracts containing IgE-BF are prepared according to methods known per se. Suitable cells are lymphocytes of human origin, particularly those which can be cultured in vitro, such as lymphoblastoma cell lines, especially continuous human B cell lines, e.g. the human B cell line RPMI 8866. Culture supernatants of such cell lines producing IgE-BF may be introduced directly, optionally after concentration, into the purification process of the invention, or may be subjected beforehand to preliminary purification by known methods, e.g. ultrafiltration, dialysis, or purification by chromatography, e.g. over DEAE-cellulose or cross-linked dextran gel such as Sephadex®.

Human colostrum preparations containing IgE-BF may be obtained in the following way: Human colostrum from healthy volunteers is collected during the first two days of postpartum, however milk collected later may also be used. The colostrum is treated with protease inhibitors, e.g. phenylmethylsulfonyl fluoride, benzamidine, $\epsilon$-aminocaproic acid and/or EDTA, then clarified, e.g. by ultracentrifugation or filtration, and acidified, e.g. with hydrochloric acid, up to about pH 4 in order to precipitate the casein. After removing the casein, e.g. by filtration or centrifugation, the clarified preparation is neutralized with buffer solution, e.g. with 2M Tris buffer, and passed through a filter system, preferably stepwise, in order to remove large molecules of over 50 KD. For example, the pores of the first filter may have a diameter of about 0.45 $\mu$m, and the filtrate thereof may then be passed through a membrane filter, e.g. an Amicon XM 50 filter, with the desired cut-off point of 50 KD. After filtration the preparation is dialyzed against distilled water and lyophilized. This colostrum preparation is preferably further purified by chromatographic methods in order to collect the polypeptides with a molecular weight of between about 10 and 30 KD. Any conventional chromatographic method may be used, such as gel filtration chromatography on agarose gel, e.g. on Sephadex® G-75. For example, the colostrum preparation is applied to an agarose gel column in a buffer solution containing a surface active compound and other adjuncts, and molecular weight fractions collected. The fractions containing the IgE-BF are those containing polypeptides of a molecular weight of about 10 to 30 KD. They are pooled, optionally concentrated, and dialyzed.

IgE-BFs are separated from other proteins and foreign substances in the solutions based on binding interactions between monoclonal antibodies specific to $Fc_\epsilon R$ (and cross-reacting with IgE-BF) and the antigenic determinants on the proteins constituting IgE-BF. For this purpose, the solutions containing IgE-BFs are brought into contact with a carrier material to which said monoclonal antibodies are bound, e.g. by a procedure known as immunoaffinity chromatography. To that end a suitable carrier material on an inorganic or organic basis, for example silicates, crosslinked agarose, dextran or polyacrylamide in suitably functionalized form, optionally having been activated, is charged in a manner known per se with the monoclonal antibodies according to the invention or their derivatives which are described hereinbelow. For example, a carrier material containing activated ester functions, for example N-hydroxysuccinimide ester groups, is suspended in an aqueous buffer solution and mixed with a solution of the monoclonal antibody, and then unbound monoclonal antibodies are washed out and unoccupied reactive sites of the carrier material are blocked, for example with a primary amine, such as ethanolamine. The carrier material is suspended in a suitable aqueous solvent, for example a salt solution, such as NaCl solution, or a buffer solution, such as phosphate-buffered NaCl solution, $NaHCO_3$ solution or 3-(N-morpholino)-propanesulphonic acid solution, and brought into contact with the solution containing IgE-BF, for example is poured into a chromatography column and the solution containing IgE-BF is introduced, pumped through the carrier material, if desired under pressure, or flows through it by gravity force. Unbound proteins and other impurities are washed away with aqueous solutions, for example buffer solutions in a pH range of from approximately pH 5 to approximately pH 9 and/or salt solutions, for example NaCl solution, optionally containing surfactants, e.g. polyethylene-sorbitan fatty acid esters. The IgE-BF bound to the antibodies on the carrier material is eluted with suitable aqueous solutions, for example buffer solutions in a pH range of from approximately pH 2 to approximately pH 5, such as glycine buffer, or pH gradients of differing composition or salt solutions, for example concentrated $NH_4SCN$ solution. The solutions containing purified IgE-BF which are obtained are optionally neutralized, and the purified IgE-BF is isolated therefrom according to methods that are known per se, for example by chromatography over Sephadex®, electrodialysis, isoelectric focussing, electrophoretic concentration and/or vacuum centrifugation.

The choice of monoclonal antibodies to be used in the immunoaffinity chromatography depends on the kind and source of IgE-BFs to be purified. For example, IgE-BF from B cell supernatants is preferably purified with the monoclonal antibodies with the designations 207.25 A.4.4/30 or 207.25 A.4.4/45, whereas IgE-BF from colostrum is preferably purified with the monoclonal antibody with the designation 208.25 D.2/94 and/or 207.25 A.4.4/30.

It should be understood that any other conventional method of isolating the IgE-BFs is comprised by the present invention.

If desired, the human IgE-BF obtained on immunoaffinity chromatography is purified further and separated into its individual optionally glycosylated proteins, for example by ion exchange chromatography, gel filtration chromatography, preparative reversed phase or hydrophobic interaction high performance liquid chromatography (HPLC) or related chromatographic methods, preparative polyacrylamide gel electrophoresis, and the like, and combinations of these purification and separation steps.

In particular, the human IgE-BF obtained on immunoaffinity chromatography is purified further by ion exchange chromatography on a weakly basic anion exchanger, e.g. diethylaminoethyl (DEAE) substituted cellulose or agarose, optionally followed by a further purification by immunoaffinity chromatography with monoclonal antibodies. The ion exchange chromatography material bearing the weakly basic anion exchanger is equilibrated in a suitable aqueous buffer solution, e.g. a buffer solution of pH 6 to pH 9, such as Tris or phosphate buffer solution, then contacted with the human IgE-BF. Preferably the chromatography is performed in a column and the solution of the human IgE-BF is pumped through the ion exchange material. Unbound proteins and impurities are washed from the column with a buffer solution and the desired optionally glycosylated peptides eluted by increasing salt concentration, e.g. by Tris buffer solution containing increasing amounts of sodium chloride. It is understood that ion exchange chromatography may be performed also on a HPLC column.

Likewise preferred is a purification of human IgE-BF with preparative reversed phase HPLC. Such a purification and separation into individual optionally glycosylated proteins is performed on silica-based carrier material bearing hydrophobic groups, e.g. alkyl groups of 2 to 20 carbon atoms or phenyl groups. Preferred is silica-based carrier material bearing lower alkyl groups, e.g. n-butyl groups. The solution of human IgE-BF is injected onto the reversed phase HPLC column and processed in aqueous acid solution, e.g. aqueous trifluoroacetic acid solution, containing increasing amounts of a polar, water-miscible organic solvent, e.g. acetonitrile, lower alcohols, e.g. methanol, ethanol or propanol, tetrahydrofuran, and the like, preferably acetonitrile.

Individual optionally glycosylated proteins are preferably obtained by preparative sodium dodecyl sulfate (SDS) polyacrylamide gel electrophoresis. A solution of human IgE-BF in a suitable buffer, e.g. Tris buffer, containing glycerol and SDS is prepared and applied to a polyacrylamide gel containing 10–15%, preferably 12%, acrylamide and up to 0.5%, e.g. around 0.3% bis-acrylamide. Gel electrophoresis is run in the usual manner together with molecular weight markers. Homogeneous molecular weight fractions are eluted from the gel and isolated in pure form, for example by ion exchange chromatography, electrophoretic concentration and/or vacuum centrifugation.

It is understood that the usual methods of dialyzing, dissolving and reprecipitating in suitable salt and/or buffer solutions and solvent mixtures may be included in the separation scheme. IgE-BF or individual glycosylated proteins may be further processed by partial or total cleavage of glycosidic linkages giving rise to other, less glycosylated proteins or unglycosylated proteins of the invention. For example, proteins of the invention are treated with enzymes cleaving glycosidic linkages, e.g. N-glycanase, neuraminidase and/or O-glycosidase, in suitable buffer solutions, e.g. phosphate or Tris buffer optionally containing adjuncts such as detergents, e.g. sodium dodecyl sulfate, TWEEN™, polyoxyethylenesorbitan NP-40 nonylphenoxy polyethoxy ethanol, complexing agents, e.g. EDTA, salts, e.g. calcium salts, reducing agents, e.g. β-mercaptoethanol, and the like. The resulting reaction products are processed as described for individual optionally glycosylated proteins or IgE-BF fragments hereinbefore.

Fragments of IgE-BF and of individual optionally glycosylated proteins of the invention are obtained by protease treatment of IgE-BF containing solutions or of individual proteins. For example, if no protease inhibitors are added to colostrum or to cell supernatants containing IgE-BF, the proteases inherently present in such solutions will cleave the IgE-BF and its individual proteins. Otherwise, a protease, e.g. papain or trypsin, may be added deliberately to solutions containing IgE-BF or to solutions containing its individual proteins.

The IgE-BF fragments are isolated and purified as described hereinbefore for IgE-BF and/or individual optionally glycosylated proteins, for example by ultrafiltration, gel filtration chromatography, immunoaffinity chromatography, ion exchange chromatography, preparative reversed phase HPLC, and/or preparative SDS polyacrylamide gel electrophoresis.

The IgE binding and IgE synthesis suppressing activity of the isolated IgE-BFs, its individual proteins and/or fragments thereof can be determined by methods known in the art, e.g. by the rosette inhibition assay, the blocking of IgE binding to anti-IgE antibodies, affinity chromatography experiments, and the like. The adsorption and elution experiments on IgE- and IgG-coupled agarose gels can be taken as specificity controls indicating that the rosette inhibition activity and the blocking of IgE binding to anti-IgE antibodies is indeed due to factors binding IgE.

The invention relates also to novel monoclonal antibodies to lymphocyte cellular receptors for IgE ($Fc_\epsilon R$) crossreacting with IgE-BF, and to derivatives thereof.

The monoclonal antibodies of the invention are e.g. detected by their ability to inhibit the binding of IgE-coated latex particles to RPMI 8866 cells expressing $Fc_\epsilon R$. The amount of inhibition is determined by counting cells bearing fluorescent labels after incubation with a solution containing monoclonal antibodies followed by fluorescent IgE-coated latex particles. The inhibition of binding of fluorescent IgE-coated latex particles to $Fc_\epsilon R$ is also shown with other B cell lines known to express $Fc_\epsilon R$.

Further, the monoclonal antibodies can be detected e.g. by their ability to bind to cells expressing $Fc_\epsilon R$. The amount of binding is determined by counting cells bearing fluorescent labels after incubation with a solution containing monoclonal antibodies followed by a solution of fluorescein-conjugated second antibody binding the monoclonal antibody of the invention, e.g. a fluorescein-conjugated goat anti-mouse immunoglobulin reagent.

The specificity of the monoclonal antibodies towards $Fc_\epsilon R$ expressed on the cell lines is demonstrated by the following observations:

(1) The intact monoclonal antibody molecules and its $F(ab')_2$ fragments block the binding of IgE to several $Fc_\epsilon R$ expressing cell lines different from that employed for the initial immunization.

(2) The monoclonal antibodies directly bind to all $Fc_\epsilon R$ expressing cell lines tested but not to several $Fc_\epsilon R$-negative cell lines.

(3) The binding of monoclonal antibodies to $Fc_\epsilon R$ expressing cells is selectively blocked by IgE but not by other classes of immunoglobulins.

(4) The monoclonal antibodies have no effect on the binding of IgG to receptors of IgG ($Fc_\gamma R$) on normal human peripheral blood mononuclear cells.

That the monoclonal antibodies specific for $Fc_\epsilon R$ cross-react with IgE-BF is shown by the fact that IgE-BFs block the binding of the monoclonal antibodies to the IgE receptors on e.g. RPMI 8866 cells.

Preferred are monoclonal antibodies to $Fc_\epsilon R$ that are crossreacting with IgE-BFs and that are produced by mouse/mouse hybridoma cells. Examples of such preferred monoclonal antibodies according to the invention are the monoclonal antibodies listed in Table I. They belong to the isotype IgG1 or IgG2b. Particularly preferred are the monoclonal antibodies produced by the clone numbers 208.25 A.4.3/135, 207.25 A.4.4/30, 207.25 A.4.4/45, 208.25 D.2.1/176, and 208.25 D.2/94.

TABLE I

Monoclonal antibodies to $Fc_\epsilon R$ and hybridoma cell lines expressing them

| Clone Number | Isotype | Light Chains |
| --- | --- | --- |
| 208.25 D.4/63 | IgG1 | Lambda |
| 208.25 D.2/94 | IgG1 | Lambda |
| 208.25 D.4.3/79 | IgG1 | Lambda |
| 208.25 A.4.2/64 | IgG1 | Lambda |
| 208.25 A.4.3/135 | IgG1 | Kappa |
| 207.25 A.4.4/30 | IgG1 | Kappa |
| 207.25 A.4.4/45 | IgG2b | Kappa |
| 207.25 A.4.4/123 | IgG2b | Kappa |
| 207.25 A.4.4/133 | IgG2b | Kappa |
| 208.25 D.2.1/176 | IgG1 | Kappa |
| 208.25 B.1.5/14 | IgG1 | Kappa |
| 208.25 A.1.5/168 | IgG1 | Kappa |
| 208.25 A.4.2/73 | IgG1 | Kappa |
| 208.25 A.4.2/79 | IgG1 | Lambda |

Hereinafter the monoclonal antibodies of the invention shown in Table I will be designated by "Mab-(number)", wherein the number corresponds to the two-digit or three-digit number behind the oblique stroke of the clone number.

Derivatives of monoclonal antibodies according to the invention are, for example, fragments, such as Fab, Fab' or $F(ab')_2$ fragments, that retain their specificity for the antigenic determinants of IgE-BF, radioactively labelled monoclonal antibodies which are labelled, for example, with radioactive iodine ($^{125}$I, $^{131}$I), carbon ($^{14}$C), sulphur ($^{35}$S), tritium ($^3$H) or the like, monoclonal antibody conjugates with biotin or avidin, or monoclonal antibody conjugates with enzymes, such as horseradish peroxidase, alkaline phosphatase, β-D-galactosidase, glucose oxidase, glucoamylase, carbonic anhydrase, acetylcholineesterase, lysozyme, malate dehydrogenase or glucose-6-phosphate dehydrogenase. Preferred derivatives are monoclonal antibodies labelled with $^{125}$iodine, antibody fragments F(ab')$_2$, and conjugates of monoclonal antibodies or F(ab')$_2$ fragments with biotin.

The monoclonal antibodies of the invention and derivatives thereof are obtained by processes known per se, characterized in that hybridoma cells secreting said monoclonal antibodies are propagated in a suitable environment and the monoclonal antibodies isolated therefrom and, if desired, the obtained monoclonal antibodies transformed into a derivative thereof. In particular, the hybridoma cells are cultivated in vitro and the monoclonal antibodies isolated from the culture supernatant, or propagated in vivo in a suitable mammal and the monoclonal antibodies recovered from body fluids of said mammal, and, if desired, the obtained monoclonal antibodies transformed into a derivative thereof.

Suitable culture media for the in vitro cultivation are standard culture media such as Dulbecco's Modified Eagle Medium or RPMI 1640 Medium, optionally replenished by a mammal serum, e.g. fetal calf serum, or other growth-sustaining supplements, e.g. 2-aminoethanol, insulin, transferrin, low density lipoprotein, oleic acid and the like, and trace elements. The isolation of the monoclonal antibodies is accomplished by precipitating the protein contained in the optionally concentrated culture supernatants by ammonium sulfate or the like, followed by purifying the immunoglobulins by standard chromatographic methods, such as gel filtration, ion exchange chromatography, chromatography on DEAE cellulose, or immunoaffinity chromatography.

In vitro production allows scale-up to give large amounts of the desired antibodies. Techniques for large scale hybridoma cultivation are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Large quantities of the desired monoclonal antibodies can also be obtained by the propagation of hybridoma cells in vivo. Cell clones are injected into syngeneic mammals, which causes antibody-producing tumors to grow. After one to three weeks the desired monoclonal antibodies are recovered from body fluids of said mammal. As an example hybridoma cells derived from Balb/c mice are intraperitoneally injected into Balb/c mice optionally pretreated with a hydrocarbon such as pristane, and after one to two weeks, ascites fluid of these mice is collected. The desired monoclonal antibodies are isolated from the body fluids by methods known per se, e.g. by precipitating the proteins with ammonium sulfate or the like, followed by purifying the immunoglobulins by standard chromatographic methods, such as gel filtration, ion exchange chromatography, chromatography on DEAE cellulose, or immunoaffinity chromatography.

Fragments of monoclonal antibodies, for example Fab, Fab' or F(ab')$_2$ fragments, which retain their specificity towards the antigenic determinants of IgE-BFs, can be obtained from the monoclonal antibodies obtained by in vitro or in vivo cultivation by methods known per se, e.g. by digestion with enzymes such as pepsin or papain and/or cleavage of disulfide bonds by chemical reduction.

Monoclonal antibodies labelled with radioactive iodine such as $^{125}$I are prepared by iodination methods known in the art, e.g. by labelling monoclonal antibodies with radioactive sodium or potassium iodide and a chemical oxidant, such as sodium hypochlorite, chloramine T or the like, or an enzymatic oxidant, such as lactoperoxidase or glucose oxidase and glucose. Radioactively labelled monoclonal antibodies of the invention are also prepared by adding radioactively labelled nutrients to the culture media of the in vitro cultivation. Such labelled nutrients contain e.g. radioactive carbon ($^{14}$C), tritium ($^3$H), sulfur ($^{35}$S) or the like, and are for example L-($^{14}$C)-leucine, L-($^3$H)-leucine or L-($^{35}$S)-methionine.

Enzyme conjugates of monoclonal antibodies of the invention are prepared by methods known in the art, e.g. by reacting a monoclonal antibody or a fragment thereof prepared as described hereinbefore with the desired enzyme in the presence of a coupling agent, e.g. glutaraldehyde, periodate, N,N'-o-phenylenedimaleimide, N-(m-maleimidobenzoyloxy)-succinimide, N-(3-(2'-pyridyldithio)-propionoxy)-succinimide, N-ethyl-N'-(3-dimethylaminopropyl)-carbodiimide or the like. Conjugates of monoclonal antibodies with avidin are obtained in like manner. Conjugates with biotin are obtained e.g. by reacting monoclonal antibodies of the invention with biotin N-hydroxysuccinimidyl ester.

Likewise, conjugates of monoclonal antibody fragments, e.g. F(ab')$_2$ fragments, with the mentioned enzymes or with biotin can be prepared.

The invention further relates to hybridoma cell lines, characterized in that they secrete monoclonal antibodies to lymphocyte cellular receptors for IgE (Fc$_\epsilon$R) crossreacting with IgE-BF.

In particular, the invention concerns cell lines which are hybrids of myeloma cells and B lymphocytes of a mammal immunized with lymphocytes expressing Fc$_\epsilon$R. Preferentially, these cell lines are hybrids of mouse myeloma cells and B lymphocytes of a syngeneic mouse immunized with lymphoblastoma cells expressing Fc$_\epsilon$R.

Particularly preferred are the hybridoma cell lines with the designation 208.25 A.4.3/135 and 208.25 D.2.1/176, which have been deposited under the Budapest Treaty on Feb. 2, 1985 at the "Collection Nationale de Cultures de Microorganismes", Institut Pasteur, Paris, under the number I-425 and I-420, respectively, the hybridoma cell lines with the designation 207.25 A.4.4/30 and 207.25 A.4.4/45, which have been deposited under the Budapest Treaty on May 29, 1985 at the "Collection Nationale de Cultures de Microorganismes", Institut Pasteur, Paris, under the number I-451 and I-452, respectively, and the hybridoma cell line with the designation 208.25 D.2/94, which has been deposited under the Budapest Treaty on Oct. 1, 1985 at the "Collection Nationale de Cultures de Microorganismes", Institut Pasteur, Paris under the number I-486. These hybridoma cell lines are hybrids of the mouse myeloma cell line NSI/1 and of B lymphocytes of the spleen of Balb/c mice immunized with viable RPMI 8866 cells. They are stable cell lines, which secrete the monoclonal antibodies with the designation Mab-135, Mab-176, Mab-30, Mab-45, and Mab-94, respectively. The cell lines may be kept in deep-frozen cultures and reactivated by thawing and re-cloning.

The invention relates also to a process for the production of hybridoma cell lines secreting monoclonal antibodies which bind to Fc$_\epsilon$R and crossreact with IgE-BF, characterized in that a suitable mammal is immunized with lymphocytes expressing Fc$_\epsilon$R, antibody-producing cells of this mammal are fused with myeloma cells, the hybrid cells obtained in the fusion are cloned, and cell clones secreting the desired antibodies are selected.

As antigens there may be used any lymphocytes expressing Fc$_\epsilon$R, also broken cells or cell wall material containing Fc$_\epsilon$R or the receptors themselves. The lymphocytes expressing Fc$_\epsilon$R may be B or also T cells, preferably lymphoblastoma cell lines or cell lines transformed with Epstein-Barr virus. Most preferred as an antigen are RPMI 8866 cells, which are human B cells of a continuous cell line. Optionally the cells are stimulated with suitable mitogens, e.g. concanavalin A, or with glycoprotein synthesis regulating compounds, e.g. tunicamycin, prior to their use as antigens. Preferred mammals for the immunization are mice, particularly Balb/c mice. The immunizations are performed e.g. by injecting viable RPMI 8866 cells three to eight times parenterally, such as intraperitoneally and/or subcutaneously, at intervals of three to five weeks, in amounts of about $10^7$ up to about $10^8$ cells.

Antibody-producing cells of the immunized mammals, preferably spleen cells, taken two to five days after the final antigen injection, are fused with myeloma cells of a suitable cell line in the presence of a fusion promoter. Several suitable myeloma cell lines are known in the art. Preferred are myeloma cell lines lacking the enzyme hypoxanthine guanine phosphoribosyl transferase (HGPRT) or the enzyme thymidine kinase (TK), which therefore do not survive in a selective culture medium containing hypoxanthine, aminopterin and thymidine (HAT medium). Particularly preferred are myeloma cells and derived cell lines that do not survive in HAT medium and do not secrete immunoglobulins or fragments thereof, such as the cell lines NSI/1-Ag4/1, X63-Ag8.653 or Sp2/O-Ag14. Fusion promoters considered are e.g. Sendai virus or other paramyxo viruses, optionally in UV-inactivated form, calcium ions, surface-active lipids such as lysolecithin, or polyethylene glycol. Preferentially, the myeloma cells are fused with a three- to tenfold excess of spleen cells from immunized mammals in a solution containing about 30% to about 60% polyethylene glycol of a molecular weight between 1000 and 4000 and, optionally, about 5% to about 15% dimethylsulfoxide.

After the fusion, the cells are resuspended and cultivated in selective HAT medium. Thereby only hybridoma cells will survive, because they combine the ability to grow and replicate in vitro inherited from myeloma cells and the missing HGPRT or TK genes essential for the survival in the HAT medium inherited from the antibody-producing spleen cells of the immunized mammals.

Suitable culture media for the expansion of hybridoma cells are the standard culture media, such as Dulbecco's modified Eagle medium, minimum essential medium, RPMI 1640 medium and the like, optionally replenished by serum, e.g. 10 to 15% fetal calf serum, amino acids, and antibiotics, e.g. penicillin and/or streptomycin. Preferentially feeder cells are added at the beginning of the cell growth, e.g. normal mouse peritoneal exsudate cells, spleen cells, marrow bone macrophages, or the like. The culture media are supplemented with selective HAT medium at regular interval in order to prevent normal myeloma cells overgrowing the hybridoma cells.

The hybridoma cell culture supernatants are screened for the desired monoclonal antibodies, preferentially with an assay wherein the inhibition of binding of IgE-coated latex particles to RPMI 8866 cells pretreated with the culture supernatants is tested. Positive hybridoma cells are cloned, e.g. by limiting dilution, preferentially twice or more. The cloned cell lines may be frozen in a conventional manner.

The monoclonal antibodies of the invention and/or their derivatives are useful for the qualitative and quantitative determination and/or purification of IgE-BF from lymphocytes or colostrum, of individual optionally glycosylated proteins and of fragments thereof.

For instance, the monoclonal antibodies or derivatives thereof, such as enzyme conjugates, biotin conjugates or radioactive derivatives, can be used in any of the known immunoassays, which rely on the binding interaction between the antigenic determinant, e.g. on Fc$_\epsilon$R or IgE-BFs, and the monoclonal antibodies. Examples of such assays are radioimmunoassays, enzyme immunoassays, immunofluorescence, latex agglutination, and hemagglutination. IgE-BFs produced by lymphocytes or isolated from colostrum can be purified by immunoaffinity chromatography with the aid of monoclonal antibodies of the invention.

In particular the invention relates to radioimmunoassays (RIA) for the determination of IgE-BFs with the aid of the monoclonal antibodies of the invention and/or radioactively labelled derivatives thereof. Any of the known modifications of an RIA can be used, for example RIA in homogeneous phase, solid phase RIA or heterogeneous RIA, single RIA or double (sandwich) RIA with direct or indirect (competitive) determination of IgE-BFs.

There is preferred an RIA in which a suitable carrier, for example the plastic surface of a titer plate or of a test tube, for example of polystyrene, polypropylene or polyvinyl chloride, glass or plastic beads, filter paper, or dextran, cellulose acetate or nitrocellulose sheets or the like, is coated with a monoclonal antibody of the invention by simple adsorption or optionally after activation of the carrier, e.g. with glutaraldehyde or cyanogen bromide, then incubated with a test or standard solution containing IgE-BF and a solution of a $^{125}$I labelled derivative of a second monoclonal antibody of the invention recognizing a different epitope of IgE-BF. It is also possible, but less desirable, to use a $^{125}$I labelled derivative of the same monoclonal antibody.

The invention relates also to enzyme immunoassays for the determination of IgE-BFs with the aid of the monoclonal antibodies of the invention and/or conjugates with enzymes or with biotin thereof, including conjugates of monoclonal antibody fragments with biotin. For example a carrier as described above for an RIA is coated with a monoclonal antibody of the invention, incubated with a test or standard solution containing IgE-BF and then with a solution of a conjugate of a different monoclonal antibody or antibody fragment with a suitable enzyme followed by a solution of an enzyme substrate that makes visible the amount of enzyme-conjugated antibody bound. In place of an enzyme-conjugated monoclonal antibody a biotin-conjugated monoclonal antibody or antibody fragment can be used together with an avidin-enzyme conjugate.

Preferred enzymes in the enzyme-immunoassays according to the invention are horseradish peroxidase which can be developed, for example, with the enzyme substrates 5-aminosalicylic acid, o-phenylenediamine, 3,3'-dimethoxybenzidine, 3,3',5,5'-tetramethylbenzidine, 2,2'-azino-bis-(3-ethylbenzothiazoline-6-sulphonic acid) or the like and hydrogen peroxide, and alkaline phosphatase which, for example, releases p-nitrophenol from the enzyme substrate p-nitrophenyl phosphate.

Particularly preferred is an enzyme immunoassay in which a suitable carrier as described above for an RIA is coated with a monoclonal antibody of the invention, then incubated with a test or standard solution containing IgE-BF and a solution of a conjugate of a monoclonal antibody of the invention or a fragment thereof with biotin, followed by a solution of an avidin-enzyme conjugate, e.g. an avidin-horseradish peroxidase conjugate, and a solution of an enzyme substrate.

The use according to the invention of monoclonal antibodies to $Fc_\epsilon R$ and their derivatives for the qualitative and quantitative determination of IgE-BF also includes other immunoassays known per se, for example immunofluorescence tests using antibody conjugates or antigen conjugates with fluorescing substances, latex agglutination with antibody-coated or antigen-coated latex particles or haemagglutination with antibody-coated or antigen-coated red blood corpuscles or the like.

The invention relates also to test kits for the qualitative and quantitative determination of IgE-BF, individual optionally glycosylated proteins and fragments thereof, characterized in that they contain monoclonal antibodies to $Fc_\epsilon R$ crossreacting with IgE-BF and/or derivatives thereof, and optionally adjuncts.

Test kits according to the invention for a radioimmunoassay contain e.g. a suitable carrier as defined hereinbefore, optionally freeze-dried or concentrated solutions of a monoclonal antibody of the invention and of a $^{125}I$ labelled, same or different monoclonal antibody of the invention, standard solutions of IgE-BF and/or individual optionally glycosylated proteins, buffer solutions, detergents preventing nonspecific adsorption and aggregate formation, pipettes, reaction vessels, calibration curves and the like.

Test kits according to the invention for an enzyme immunoassay contain e.g. a suitable carrier as defined hereinbefore, optionally freeze-dried or concentrated solutions of a monoclonal antibody of the invention and of a conjugate of a monoclonal antibody or antibody fragment of the invention with an enzyme or with biotin and, when a biotin conjugate is used, of an avidin-enzyme conjugate, standard solutions of IgE-BF and/or individual optionally glycosylated proteins, buffer solutions, enzyme substrates in solid or dissolved form, detergents preventing non-specific adsorption and aggregate formation, pipettes, reaction vessels, calibration curves and the like.

The invention further relates to the use of the purified IgE-BFs, individual optionally glycosylated proteins, and fragments thereof for the treatment or prevention of allergic conditions in patients being allergic against all kinds of antigens, for example pollens, cat danders, house dust mites, and the like. Particularly important would be the treatment of high risk patients during critical periods, including especially high risk new-borns which are not breast-fed. The IgE-BFs of the present invention are administered enterally, for example nasally, rectally or orally, or parenterally, for example, intramuscularly, subcutaneously or intravenously, usually in dosage unit forms such as tablets, dragees, ampoules, vials, or suppositories. The amount of purified IgE-BFs, its individual optionally glycosylated proteins or fragments thereof to be administered depends on the weight and general condition of the patient, the severity of the disease, the mode of administration and has to be based on the judgement of the physician. In general a dose of between about 100 μg and about 5000 μg per kg bodyweight and day may be administered.

The invention further relates to pharmaceutical preparations containing the IgE-BFs, its individual optionally glycosylated proteins or fragments thereof in an antiallergically effective amount optionally in conjunction with conventional pharmaceutically acceptable carriers that are suitable for oral, rectal, nasal or parenteral, i.e. intramuscular, subcutaneous or intraperitoneal, administration and that do not deleteriously interact with the active ingredients.

There are suitable tablets, capsules, vials containing a solid powder, or nebulizers, sprays, vials, ampoules and the like containing infusion solutions, preferably aqueous solutions or suspensions, it being possible to prepare these before use, for example from lyophilized preparations that contain the active ingredient alone or together with a carrier, such as mannitol, lactose, glucose, albumin and the like. The pharmaceutical preparation may be sterilized and, if desired, mixed with adjuncts, for example preservatives, stabilisers, emulsifiers, solubilisers, buffers and/or salts for regulating the osmotic pressure. Sterilization can be achieved by sterile filtration through filters of small pore size (0.45 μm diameter or smaller) after which the preparation can be lyophilized, if desired. Antibiotics may also be added in order to assist in preserving sterility.

The pharmaceutical preparations according to the present invention are dispensed in unit dosage forms, for example ampoules, comprising 1 to 2000 mg of a pharmaceutically acceptable carrier per unit dosage and about 1 to 100 mg, preferably about 2 to 50 mg, of the active ingredient, i.e. the purified IgE-BF or its individual proteins per unit dosage.

The invention also relates to a method for producing a pharmaceutical preparation, characterized in that the purified IgE-BF, its individual optionally glycosylated proteins or fragments thereof are admixed with a pharmaceutically acceptable carrier.

The pharmaceutical preparations are produced in a manner known per se, for example by conventional mixing, dissolving, lyophilizing and the like processes and contain from about 0.1% to 100%, especially from about 1% to 50% of the active substances.

The use of the new proteins for the prophylactic and therapeutic treatment of the human body is also an object of the present invention.

SHORT DESCRIPTION OF THE FIGURES

FIG. 1 shows fluorescence histograms of RPMI 8866 cells reacted with either (A) IgE-coated latex particles or (B) fetal calf serum coated latex particles. The extent of labelling is quantified by the number of cells per channel in function of the channel number, which itself is a function of the logarithm of the fluorescence intensity. Details are given in Example 3.

FIG. 3 shows fluorescence histograms demonstrating the ability of IgE (at concentrations of 10 or 100 μg/ml) to inhibit the binding of four different monoclonal antibodies to RPMI 8866 cells, whereas IgG has no effect. Details are given in Example 7.

EXAMPLES

Figure 1:
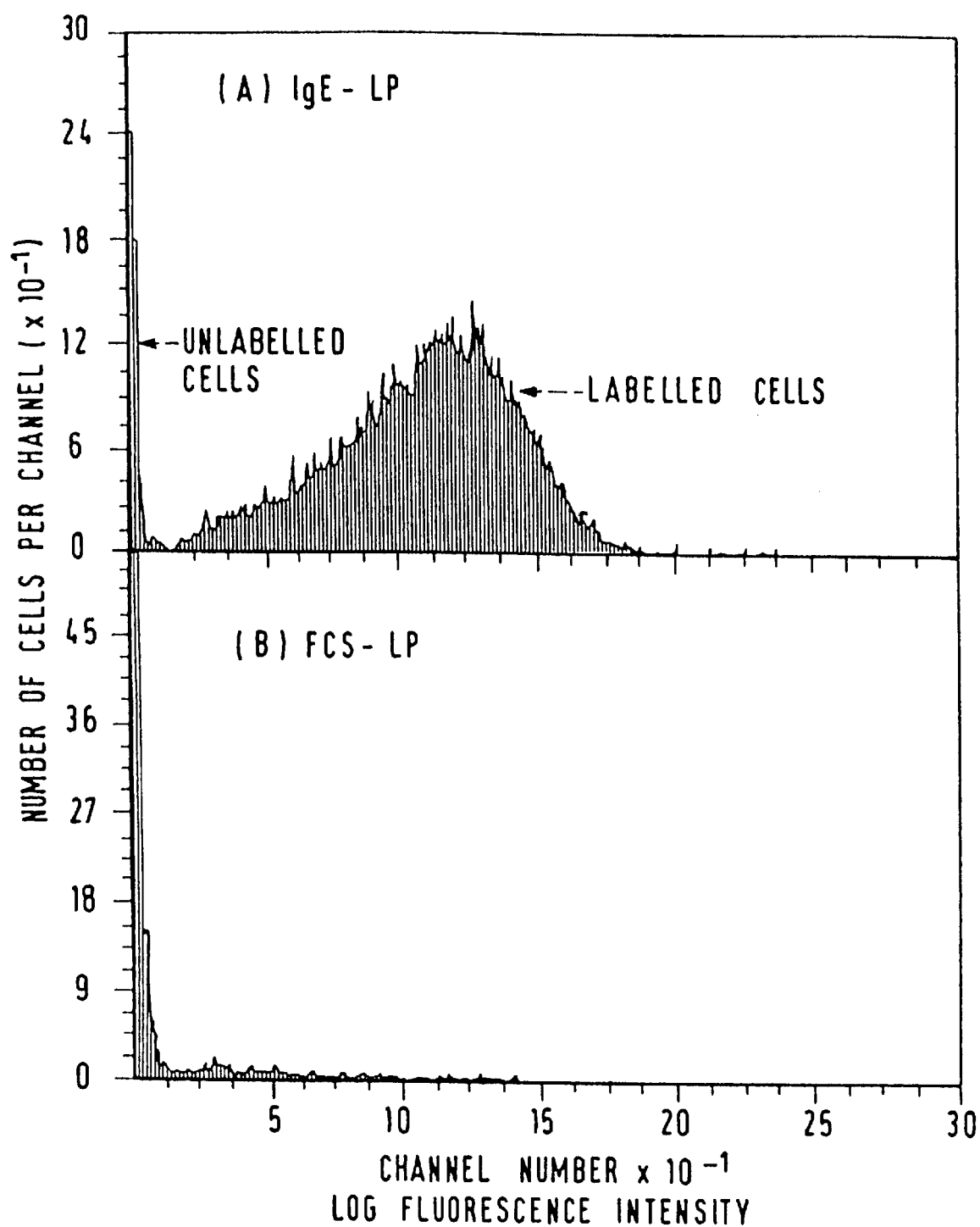

The following examples describe the present invention in more detail, however, they should not be construed as a limitation thereof.

The abbreviations used in the Examples have the following meanings:
BSA bovine serum albumin
cpm counts per min
EBV Epstein-Barr virus
F(ab')$_2$ immunoglobulin fragment (ab')$_2$
Fc$_\epsilon$R receptor for IgE
Fc$_\gamma$R receptor for IgG
FCS fetal calf serum
FCS-LP FCS-coated latex particle
HAT hypoxanthine/aminopterin/thymidine
HBSS Hank's balanced salt solution
HEPES N-2-hydroxyethylpiperazine-N'-2-ethanesulfonic acid
HPLC high pressure liquid chromatography
HT hypoxanthine/thymidine
IgE immunoglobulin E
IgE-BF IgE binding factor
IgE-LP IgE-coated latex particle
IgE PS IgE myeloma protein (isolated from patient PS)
IgG immunoglobulin G
Mab monoclonal antibody (antibodies)
PEG polyethylene glycol
PBS phosphate buffered saline
RIA radioimmunoassay
SD standard deviation
SDS sodium dodecyl sulfate
SDS-PAGE SDS polyacrylamide gel electrophoresis
TFA trifluoroacetic acid
Tris tris(hydroxymethyl)aminomethane

Example 1

Preparation of hybridoma cells

BALB/c mice are immunized by three intraperitoneal injections of $5 \times 10^7$ viable RPMI 8866 cells (received from Dr. P. Ralph, Sloan-Kettering Research Institute, N.Y., USA) in PBS at 4 week intervals. Individual mouse serum samples collected 2 days after the last injection are tested for anti-Fc$_\epsilon$R activity using the procedure of Example 3. Spleen cells from two animals displaying the highest titers are pooled and used for fusion the next day. The spleens are teased and for each fusion, $1 \times 10^8$ washed spleen cells are pelleted with $25 \times 10^6$ NSI/1-Ag4/1 mouse myeloma cells (obtained from the American type tissue culture collection) for 5 min at 350×g. The cellular pellet is gently resuspended for 30 sec in 2 ml polyethylene glycol solution (PEG-1540, Baker) consisting of 20 g PEG dissolved in 28 ml RPMI 1640 medium (Gibco) containing 15% (v/v) dimethylsulfoxide.

5 ml of RPMI/c medium [RPMI 1640 medium supplemented with 1% penicillin-streptomycin (Gibco), 1% L-glutamine (Gibco) and 15% (v/v) FCS (Gibco)] is added dropwise over a period of 90 sec followed by the rapid addition of an additional 5 ml. The cellular suspension is mixed by inverting the tube, allowed to stand for 2.5 min and centrifuged at 350×g for 5 min. The pellet is resuspended in 5 ml RPMI/c medium and 50 µl aliquots are dispensed into each well of 4 Costar # 3596 24-well plates also containing $1 \times 10^6$ normal BALB/c spleen cells in 1 ml HAT-medium (RPMI/c supplemented with 40 µM 2-mercaptoethanol, 100 µM hypoxanthine, 10 µM aminopterin and 1 µM thymidine). All cultures are maintained by alternate addition or replacement of HAT medium every few days as required, starting on the 5th day following fusion. After 14 days HAT is replaced by HT medium and after 28 days by RPMI/c. Supernatants of individual wells (192 cultures) are screened for anti-Fc R antibodies as described in Example 3, one and two weeks after the fusion. 21 cultures producing the desired antibodies are cloned by limiting dilution; they are diluted in RPMI/c to a concentration of 10 viable cells/ml and 50 µl aliquots of these suspensions are placed into wells of 96-well plates (Linbro #76-003-05, Flow Labs), containing 100 µl HT medium and $1 \times 10^5$ normal BALB/c spleen cells. The wells are examined microscopically to ensure that the growing cultures are monoclonal. Samples of supernatants taken therefrom are tested for antibody activity; positive cultures are selected and expanded in larger culture vessels. 14 monoclonal cell lines secreting antibodies of the required specificity are finally obtained; they are listed in Table I.

Example 2

Isolation and purification of monoclonal antibodies

Balb/c mice are pretreated intraperitoneally with 0.5 ml pristane (Aldrich). 2 weeks later, $5 \times 10^6$ cloned hybridoma cells are injected intraperitoneally. After 8–10 days ascites fluid is collected, centrifuged at 800×g and stored at −20° C. Defrosted ascites fluid is centrifuged at 50,000×g for 60 min. A fat layer floating on the surface is carefully removed, and the protein concentration is adjusted to a concentration of 10–12 mg/ml. Crude immunoglobulin is precipitated by dropwise addition of 0.9 volume equivalents of saturated ammonium sulphate at 0° C., then dissolved in 20 mM Tris-HCl/50 mM NaCl (pH 7.9) and dialyzed against the same buffer. An immunoglobulin G fraction is obtained by DEAE-D52 cellulose (Whatman) chromatography using a buffer gradient system of 20 mM Tris-HCl/25–400 mM NaCl, pH 7.9. The immunoglobulin G is again precipitated with ammonium sulphate and dissolved in PBS at a concentration of 10 mg/ml.

It is also possible to obtain monoclonal antibodies by in vitro propagation: A preculture containing the hybridoma cells is cultivated at physiological temperature (ca. 37° C.) in culture medium (RPMI 1640 supplemented with 10% FCS) to a cell density of $5 \times 10^5 10^6$ cells/ml. The complete preculture is transferred into Bellco spinner-bottles graduated to a volume of 3000 ml. Culture medium is added to give a final volume of 1500 ml. The culture is stirred for two to three days at 30 rpm in an air atmosphere enriched with 5% $CO_2$ at physiological temperature. The volume of the culture is increased to 3000 ml with more culture medium. The culture is cultivated for another 7–10 days using the above culturing conditions. When 95% of the cells are dead, the medium containing the cells is centrifuged at 1000×g for 20 min at 4° C. The supernatant is filtered (0.2 µm pore size) under sterile conditions. The crude immunoglobulin is obtained by addition of saturated ammonium sulfate, then purified as described hereinbefore.

The purified Mabs are routinely characterized by SDS-PAGE and by Ouchterlony analysis with sheep antisera to mouse Ig subclasses. The subclasses are listed in Table I.

Example 3

Detection of antibodies to $Fc_\epsilon R$ by flow cytometry

Antibodies to the $Fc_\epsilon R$ are detected by their ability to inhibit the binding of IgE-coated latex particles (IgE-LP) to RPMI 8866 cells. For screening, hybridoma supernatants (100 μl) are placed into microtiter wells (96-well V-bottom, Flow Labs #76-321-05) containing $2\times10^5$ RPMI 8866 cells, and gently agitated for 30 min at 20° C. The plates are centrifuged at 300×g for 6 min and the cell pellets resuspended and washed twice with RPMI medium supplemented wih 10% FCS and buffered with 10 mM HEPES pH 7.2 (H-RPMI). IgE-LP (100 μl/well), prepared by coating fluorescent MX-Covaspheres 0.7 μM (Covalent Technology Corp., Ann Arbor, USA) with IgE PS and blocking residual binding sites with FCS as described by M. Sarfati et al., Immunology 53, 783 (1984), are mixed with the cells, transferred to flat-bottomed 96-well microtiter plates (Costar #3590), and cosedimented at 300×g for 15 min at 20° C. The plates are then allowed to incubate undisturbed for 30 min at 20° C., after which time each cell monolayer is resuspended and overlayed onto 300 μl FCS contained in a conical 0.5 ml microcentrifuge tube (Fisher Scientific #5-407-6). The tubes are centrifuged at 125×g for 8 min and the supernatants containing the unattached IgE-LP removed by aspiration. The cell pellets are each suspended in approximately 300 μl H-RPMI and stored on ice until analyzed. Control samples include supernatant from NSI/1 cells or RPMI/c in lieu of hybridoma supernatants (positive control) or FCS-coated LP (FCS-LP) in lieu of IgE-LP (negative control).

Flow cytometric analysis is performed on a fluorescence-activated cell sorter (EPICS V™, Coulter Electronics) with fluorescent determinations being gated on both forward angle and 90 degree light scatter characteristics as described by M. Sarfati et al., Immunology 53, 783 (1984). Samples are analyzed at 2 min intervals with each fluorescence histogram being based on 10,000 gated counts.

FIG. 1 shows fluorescence histograms with positive and negative control, demonstrating that 80–90% of RPMI 8866 cells are labelled with 4 or more beads (channel 15 or higher) using IgE-LP as compared with 1–3% labelling using FCS-LP.

Figure 2:
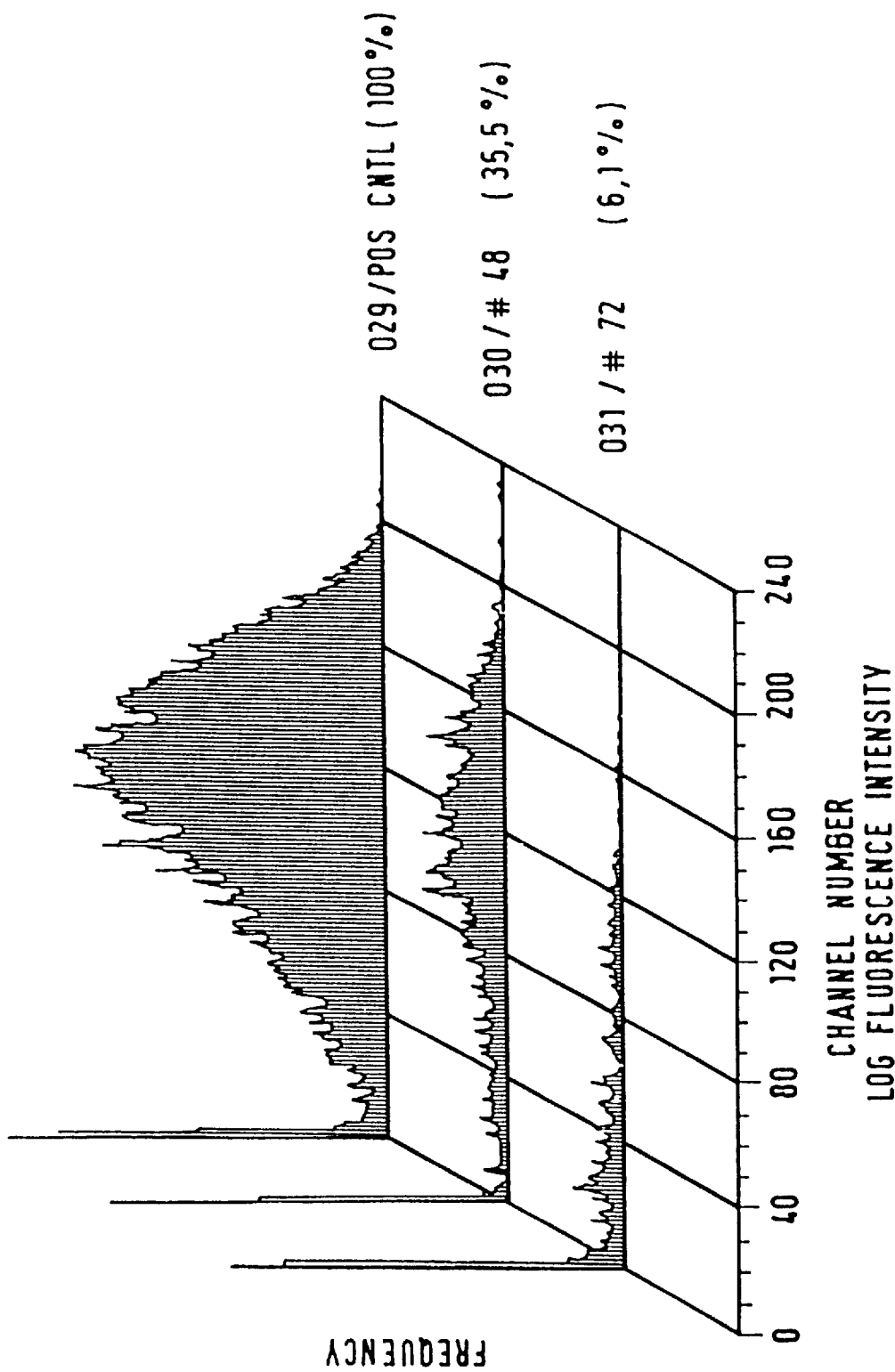
FIG. 2 shows representative fluorescence histograms indicating the presence of antibodies to $Fc_\epsilon R$ in selected hybridoma cell culture supernatants. Details are given in Example 3.
Figure 4A:
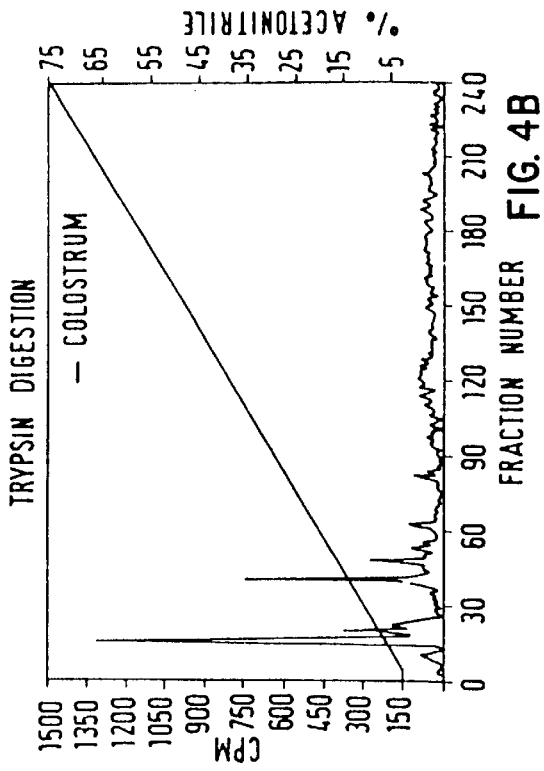
FIG. 4 shows the analysis result of a reversed phase HPLC of reaction products obtained on papain and trypsin digestion of radiolabeled 25–28 KD protein from RPMI 8866 cells and from colostrum, respectively. This experiment demonstrates the identity of processed 25–28 KD protein from either source.
Figure 4B:
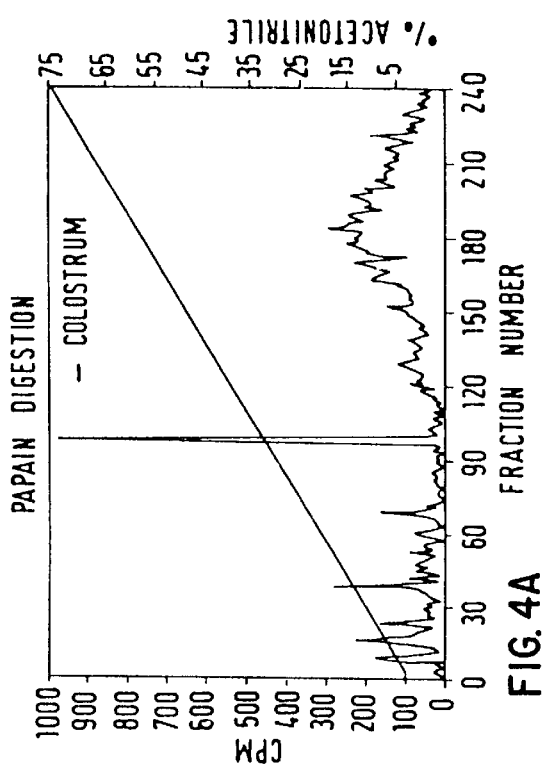
Figure 4C:
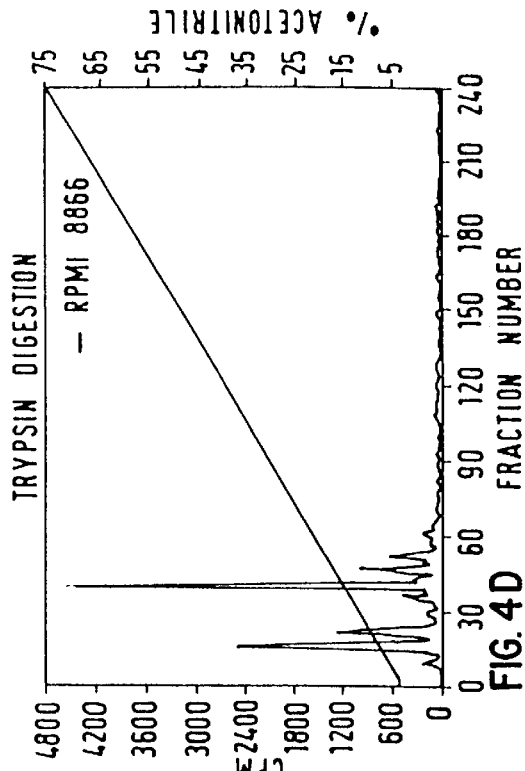
Figure 4D:
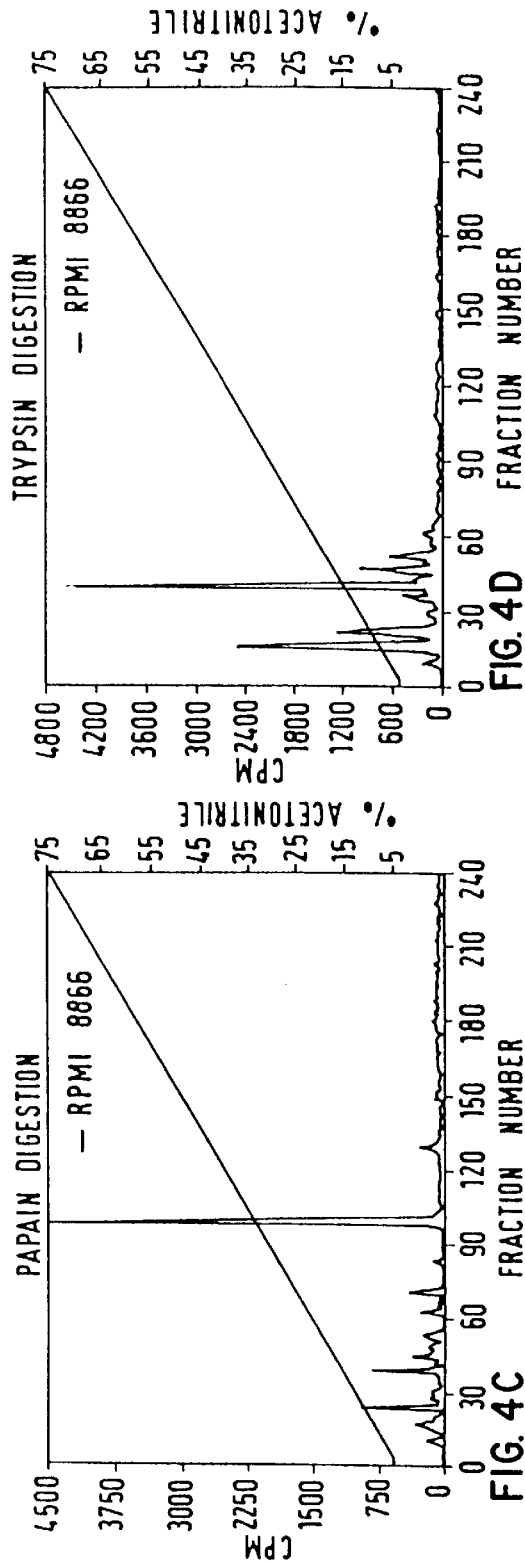

FIG. 2 illustrates the screening method and shows fluorescence histograms with positive control (029/POS CNTL) and hybridoma supernatants containing antibodies (030/#48 and 031/#72), demonstrating the inhibition of fluorescence labelling by antibodies binding to $Fc_\epsilon R$. The percentages in parentheses are normalized total fluorescence values, which are defined as the product of the mean channel number of labelled cells times number of labelled cells.

Example 4

Detection of antibodies to $Fc_\epsilon R$ by an indirect immunofluorescence assay $2\times10^5$ RPMI 8866 cells are incubated with hybridoma supernatants or other solution of Mabs for 30 min at 4° C. in a total volume of 0.2 ml H-RPMI. Following two washes with H-RPMI, 200 μl of a fluorescein-conjugated goat anti-mouse Ig reagent (GAM-FITC™, Coulter Immunology) are added and reacted for 30 min at 4° C. After an additional two washes with H-RPMI, the cells are resuspended in 300 μl H-RPMI and analyzed by flow cytometry as described in Example 3.

Example 5

Further characterization of Mab binding to $Fc_\epsilon R$

5.1 Inhibition of IgE binding to EBV-transformed B cells

The ability of the monoclonal antibodies of the invention to inhibit the binding of IgE to its receptor is not restricted to the RPMI 8866 cell line, but can be shown also with other B cell lines known to express $Fc_\epsilon R$, e.g. the Epstein-Barr virus transformed B cell lines EBV-RCA, EBV-JG and EBV-WL [M. Sarfati et al., Immunology 53, 207 (1984)]. The experiments are performed as described for RPMI 8866 in Example 3. The results for one of the monoclonal antibodies, Mab-135, are shown in Table II.

TABLE II

Blocking by Mab-135 of IgE binding to four different cell lines expressing $Fc_\epsilon R$ [a]

| Cells pre-incubated with: | Cell lines [b] | | | |
|---|---|---|---|---|
| | RPMI 8866 | EBV-RCA | EBV-JG | EBV-WL |
| Medium | 92.9 | 69.0 | 76.6 | 69.7 |
| Mab-135 [c] | 1.5 | 0.2 | 0.3 | 0.3 |
| Mouse IgG [d] | 91.2 | 55.7 | 80.7 | 63.1 |

[a] Percentage of cells labelled with IgE-LP following pre-incubation with either Mab-135, mouse IgG or medium.
[b] The cell lines are obtained as described by M. Sarfati et al., Immunology 53, 207 (1984). The cell lines are cultured in RPMI 1640 supplemented with 15% FCS, 1% penicillin-streptomycin solution (Gibco) and 1% L-glutamine.
[c] Employed at 0.5 μg/ml (final concentration).
[d] Employed at 100 μg/ml (final concentration).

The results of the experiments shown in Table II indicate that the monoclonal antibody completely blocks the binding of IgE to each B cell line. The data also suggest that the inhibition is not mediated by its Fc region, because a large excess of mouse IgG can not mimic the inhibitory activity of Mab-135. A more direct demonstration that the Mab is reacting with $Fc_\epsilon R$ via its Fab region and not by Fc binding is obtained in an experiment, wherein the activities of intact Mab-135 and its F(ab')$_2$ fragment (Example 6) are compared. It is observed that the F(ab')$_2$ portion of Mab-135 is as effective as Mab-135 itself in blocking the binding of IgE-LP to RPMI 8866 cells: RPMI 8866 cells are pre-incubated with either medium, intact Mab-135 (0.5 μg/ml), or F(ab')$_2$ fragments of Mab-135 (0.5 μg/ml) and reacted subsequently with IgE-LP. The percentages of cells labelled are 89.3, 0.4 and 0.4% respectively. 0.5% of cells are labelled on reaction with FCS-LP in place of IgE-LP (negative control).

5.2 Binding of Mab to $Fc_\epsilon R$ positive and negative cell lines

The specificity of e.g. Mab-135 for $Fc_\epsilon R$ is further evaluated by testing its direct binding to different cell lines previously tested for their expression of $Fc_\epsilon R$ (Table III). Mab-135 is employed at a concentration determined in initial titration experiments to label more than 90% of RPMI 8866 cells. Three cell lines do not react either with IgE-LP or with Mab-135, whereas 181.21.2.20 AR cells react with both. Mouse IgG, employed as negative control, does not bind to any of the cell lines. Thus, a direct concordance between IgE and Mab-135 binding is demonstrated.

TABLE III

Binding of Mab-135 to cell lines expressing $Fc_\epsilon R$

| | % Positive [a] | | | |
|---|---|---|---|---|
| Cell lines [b] | IgE-LP | Mab-135 | FCS-LP [c] | Mouse IgG [c] |
| RPMI 8866 | 95.0 | 93.6 | 1.3 | 1.2 |
| MOLT 4 | 0.51 | 2.3 | 0.06 | 1.3 |
| RPMI 8226 | 0.58 | 0.33 | 0.13 | 0.47 |
| CCL85 | 0.73 | 1.29 | 0.41 | 1.36 |
| 181.21.2.20 AR | 12.1 | 18.0 | 0.45 | 2.8 |

[a] Cells are incubated either with IgE-LP (Example 3) or monoclonal antibody and GAM-FITC ™ (Example 4) followed by flow cytometry analysis.
[b] The MOLT 4 human T cell line and the RPMI 8226 and the CCL85 B cell lines are obtained from the American type tissue culture collection. The non-secreting human B cell line 181.21.2.20 AR is prepared by fusing CCL 85 cells with peripheral blood mononuclear cells from a patient with monocytic leukemia [M. Sarfati et al., Immunology 53, 207 (1984)]. All the cell lines are cultured as described under Table II.
[c] FCS-LP and mouse IgG serve as controls for IgE-LP and Mab-135, respectively.

5.3 Capping experiments

RPMI 8866 cells are incubated under capping conditions with Mab-135 or any other Mab of Table I, subsequently washed, and finally reacted with IgE-LP. After 60 min incubation at 37° C. in the presence of 0.5 μg/ml of Mab, the cells have completely lost their capacity to bind to GAM-FITC™ (Example 4), indicating the efficiency of the capping, but also to IgE-LP (Table IV). In control experiments, it is found that preincubation of RPMI 8866 cells under capping conditions with I2, B1 or OKT9 monoclonal antibodies (purchased from Becton, Dickinson and Ortho), which are commercial antibodies known to react strongly with RPMI 8866, have no effect on the subsequent binding of IgE-LP.

TABLE IV

Capping of $Fc_\epsilon R$ by Mab-135

| RPMI 8866 cells pre-incubated with: | Cells expressing $Fc_\epsilon R$ (% ± SD)[a] |
|---|---|
| Medium | 78.4 ± 3.5 |
| Mab-135[b] | 1.6 ± 0.4 |
| B1 | 77.1 ± 0.5 |
| I2 | 83.8 ± 0.8 |
| OKT9 | 76.8 ± 2.2 |

[a] Percentage of cells reactive with IgE-LP, based on duplicate histograms of 20,000 cells.
[b] Employed at a final concentration of 0.5 μg/ml.

Example 6

Preparation of immunoglobulin fragments F(ab')$_2$

Mabs isolated from ascitic fluid (Example 2) are digested with the enzyme pepsin (5% w/w) for 20 hr at 37° C. This digest is fractionated by gel filtration (Sephadex® G-200, Pharmacia) and the fractions containing F(ab')$_2$ fragments further depleted of residual undigested IgG by absorption with Sepharose-coupled goat antibodies to mouse IgGl. The purified Ig and their fragments are tested by SDS-PAGE; the preparations are stained with Coomassie blue.

Example 7

Inhibition by IgE of the binding of Mab to RPMI 8866 cells

The preincubation of RPMI 8866 cells with IgE saturates the $Fc_\epsilon R$ and inhibits the subsequent binding of Mab to the cells, demonstrating the specificity of the Mabs to $Fc_\epsilon R$. These assays are performed using indirect immunofluorescence (Example 4) by employing limiting concentrations of Mabs (0.1 μg/ml) which label from 35–70% of the RPMI 8866 cells.

FIG. 3 shows that the binding of four different Mabs (0.1 μg/ml) to RPMI 8866 cells is inhibited in a dose-dependent fashion after preincubation of the cells with either 10 or 100 μg/ml of IgE PS (IgE 10, IgE 100) ; on the other hand no inhibition of labelling is evident following preincubation with 100 μg/ml of human IgG (IgG 100). Each histogramm is based on the analysis of 20,000 cells.

In other similar experiments it is found that IgA, IgM and IgD employed at concentrations ranging from 100 to 500 μg/ml have no effect on the binding of Mab-135 to either RPMI 8866 cells or the EBV cell lines expressing $Fc_\epsilon R$ of Example 5 (Table II).

Example 8

Influence of Mab on the binding of IgG to $Fc_\gamma R$

In these assays, peripheral blood mononuclear cells are preincubated with 10 μg/ml of Mab-135, and subsequently washed and rosetted with IgG-coated ox erythrocytes. In the absence of Mab, 11.4±4.5% of the cells form rosettes as compared to 11.1±3.4% in the presence of 10 μg/ml of Mab-135 (mean±1 SD of four experiments).

Example 9

Inhibition by IgE-BF of the binding of Mab to RPMI 8866 cells

Bovine erythrocytes are coated with Mabs, e.g. Mab-135, as described by S. Romagnani et al., J. Immunol. 124, 1620 (1980). 15 μl of 2% Mab-135 coated erythrocytes in Hanks' balanced salt solution containing 3% BSA (HBSS-BSA) are incubated for 60 min at 4° with 30 μl of IgE-BF containing cell-free supernatant of RPMI 8866 cells concentrated 10 fold, or with HB101 medium as negative control, with intermittent agitation. 15 μl of RPMI 8866 cells ($10^7$ cells/ml in HBSS-BSA) are added and, after 15 min at 4°, the mixture is centrifuged at 90×g for 5 min at 4° and kept at 0° for 2 hr. 200 μl of HBSS-BSA containing acridine orange are added to the pellet and the cells are gently resuspended before being examined under a fluorescence microscope. The background is determined with BSA-coated erythrocytes and is subtracted for the calculation of the percentages of cells forming rosettes. Rosettes are counted on 500–600 cells in duplicate or triplicate preparations.

TABLE V

Influence of IgE-BF containing cell-free supernatant on Mab-135 binding to RPMI 8866 cells

| Experiment No. | % of cells forming rosettes with E-Mab-135[a] | | % rosette inhibition |
|---|---|---|---|
| | E-Mab-135 pre-incubated with medium | E-Mab-135 pre-incubated with CFS[b] | |
| 1 | 85.6 | 64.4 | 24.7 |
| 2 | 61.5 | 29.0 | 52.8 |
| 3 | 48.0 | 23.7 | 50.6 |
| 4 | 76.0 | 55.0 | 28.4 |

[a]E-Mab-135 refers to bovine erythrocytes coated with Mab-135.
[b]CFS refers to cell-free supernatant containing IgE-BFs.

Example 10

Preparation of immunoaffinity-gel for the purification of IgE-BFs

Affi-Gel®10 (Bio-Rad) is washed as directed by the manufacturer with cold distilled water and coupling buffer pH 8.0 (0.1M NaHCO$_3$ solution). A 50% strength suspension of the gel in coupling buffer (2 ml) is introduced into a plastic tube and mixed with the same volume of a solution that contains 10 mg of Mab-30, and the mixture is rotated for 4 hours at room temperature. The gel is then washed with coupling buffer. In order to block the active sites that are still free, the gel is treated for 2 hours at room temperature with 0.1 ml of 1M ethanolamine-HCl, pH 8.0, then washed with PBS containing 10 mmol of sodium azide and kept therein at 4° C.

An immunoaffinity gel containing Mab-45, Mab-94 or Mab-135 is prepared likewise.

Example 11

Purification of IgE-BF from human B-cell supernatants by immunoaffinity chromatography Culture supernatant from RPMI 8866 cells is concentrated 100-fold on Amicon® YM5 membrane filters. 70 ml of this solution are filtered through a 2 ml column of Mab-30- or Mab-45-Affigel (Example 10) at a flow rate of 5 ml/hr. The gel is washed successively with 20 volumes PBS supplemented with 0.5M NaCl and 0.05% TWEEN 20™, polyoxyethylenesorbitan, 5 volumes PBS and 5 volumes NaCl 0.9%. The protein content of the flow-through is monitored by on-line absorbance at 280 nm by means of a Uvicord® spectrophotometer to ensure complete removal of unbound proteins. The column is then eluted with 8 ml 0.1M glycine-HCl/0.1M NaCl, pH 2.6, and the protein-containing fractions combined, neutralized with 1M Tris, and dialyzed against distilled water.

Concentrated solutions of purified IgE-BF are obtained by treatment with a ISCO electrophoretic concentrator Model 1750 (ISCO Inc.) and a Spectrapor® membrane (Spectrum Medical Industries) with 3.5 KD cut-off. The solutions are dialyzed against 25 mM ammonium acetate, pH 8.3, and thereby concentrated to a volume of 0.2 ml.

This purified IgE-BF is analyzed in the following way: Fractions are incubated with Laemmli buffer containing 1% SDS and 5% 2-mercaptoethanol, then separated into individual proteins by 12% SDS-PAGE and silver staining as described in the BioRad manual. Proteins with approximate molecular weight of 12, 16, 25–28, 45 and 60 KD are detected. They are transferred electrophoretically (4 hrs at 0.21A, transfer buffer: 25 mM Tris, pH 8.3, 192 mM glycine, 20% (v/v) methanol) to a nitrocellulose membrane. The membrane is blocked with Tris-buffered saline containing 10% FCS. Strips are cut and reacted individually with Mab-30, 135 and 64, each at 10 μg/ml. After 6 hrs incubation the strips are washed and reacted overnight with horseradish peroxidase goat anti-mouse IgG. The strips are washed and developed with 4-chloro-1-naphthol (peroxidase substrate) as detailed in the BioRad instruction manual. The Mab-30, 135 and 64 each react with the 25–28 KD and irregularly with the 45 KD protein band.

Example 12

Further purification of IgE-BF from B-cell supernatants and isolation of the 25–28 KD protein 12.1 Ion exchange chromatography and immunoaffinity chromatography Purified IgE-BF of Example 11 in 0.05M Tris-HCl, pH 7.4, is added to a TSK 545 DEAE column (LKB). The column is washed with excess 0.05M Tris-HCl and the product eluted with a gradient of 0 to 0.5M NaCl. The 25–28 KD protein elutes at a concentration of 0.15M. The product obtained is purified once more on a column of Mab-30-Affigel and analyzed by SDS-PAGE as described in Example 11.

12.2. Reversed phase HPLC

Purified IgE-BF of Example 11 in 0.1% TFA/5% acetonitrile is processed on a preparative Hi-Pore®RP-304 HPLC column (Bio-Rad) with a gradient of 5 to 75% acetonitrile in 0.1% TFA. The 25–28 KD protein elutes at a concentration of 31%. It is homogeneous when analyzed by SDS-PAGE as described in Example 11.

12.3. Preparative SDS polyacrylamide gel electrophoresis

Purified IgE-BF of Example 11 is dissolved in sample buffer [U.K. Laemmli & M. Favre, J. Mol. Biol. 80, 575 (1973)]. The slab gels (1.5 mm thick and 110 mm long) are prepared as described by Laemmli & Favre. The separating gel contains 12% acrylamide and 0.32% bis-acrylamide. At the end of the electrophoresis the proteins are visualized by dipping the gel into ice-cold 0.25 mM KCl. The gel contains three closely spaced bands in the molecular weight range of 25–28 KD. The piece of gel containing the center band is excised and washed extensively. An ISCO sample concentrator (Model 1750) is used to elute the proteins from the gel piece, as described by A. J. Brown & J. C. Bennett [Methods in Enzymology 91, 450 (1983)]. The protein is dialyzed to remove glycine. SDS is removed by ion-pair extraction as described by W. H. Konigsberg & L. Henderson [Methods in Enzymology 91, 254 (1983)].

Example 13

Determination of amino acid composition of the 25–28 KD protein

The 25–28 KD protein purified by SDS-PAGE according to Example 12.3 (48 pMol, 1.2 μg) is lyophilized, then dissolved in 6N HCl and boiled at 110° C. under vacuum for 24 hrs. The amino acids are derivatized with 4'-dimethylamino-azobenzene-4-sulfonyl chloride in sodium bicarbonate buffer, and 5% of the mixture (corresponding to 2.4 pMol per amino acid) analyzed on a Merck Lichrosphere®100 CH-18/2 HPLC column using a Waters instrument following a procedure of J. Y. Chang, R.

Knecht & D. G. Braun [Methods of Enzymology, Vol. 91, 41–48 (1983)].

The results are collected in Table VI. Due to an excess of free glycine (1.2 nMol) in the protein sample, the corrected value for Gly in Table VI is less reliable. The amount of amino acid residues is calculated on the basis of a total of 215 amino acids corresponding to a molecular weight of 25 KD.

TABLE VI

Amino acid composition of the 25-28 KD protein

| Amino acid | | pMol found | approximate number of amino acids[a] | actual range of amino acids |
|---|---|---|---|---|
| Asx | (aspartic acid/asparagine) | 50.8 | 21 | 19–23 |
| Glx | (glutamic acid/glutamine) | 67.2 | 28 | 25–31 |
| Ser | (serine) | 57.7 | 24 | 22–26 |
| Thr | (threonine) | 22.0 | 9 | 8–10 |
| Gly | (glycine) | 50[b] | 20 | 15–25 |
| Ala | (alanine) | 43.9 | 18 | 16–20 |
| Arg | (arginine) | 26.8 | 11 | 10–12 |
| Pro | (proline) | 34.9 | 14 | 13–16 |
| Val | (valine) | 26.6 | 11 | 10–12 |
| Met | (methionine) | 9.3 | 4 | 3–5 |
| Ile | (isoleucine) | 18.4 | 8 | 7–9 |
| Leu | (leucine) | 36.5 | 15 | 13–17 |
| Trp | (tryptophan) | not detected | 0 | 0 |
| Phe | (phenylalanine) | 18.0 | 8 | 6–9 |
| Cys | (cysteine) | 7.6 | 3 | 3–4 |
| Lys | (lysine) | 22.2 | 9 | 8–10 |
| His | (histidine) | 11.4 | 5 | 4–5 |
| Tyr | (tyrosine) | 16.5 | 7 | 6–8 |

[a] Based on 215 amino acids corresponding to molecular weight of 25 KD
[b] Corrected value due to free glycine in the protein sample. Actual value 109 pMol.

Example 14

Preparation of fragments of the 25–28 KD protein 14.1 By simple storage

Purified 25–28 KD protein is kept at 4° C. for a few weeks in the absence of protein inhibitors. The sample is separated by 12% SDS-PAGE as described in Example 11. In addition to the 25–28 KD protein, a 14–16 KD protein is detected. Both proteins react with Mab-30 when transferred to nitrocellulose.

14.2. By digestion with papain 0.1 ml of immobilized papain (Pierce Chemicals, 7 BAEE units per ml of settled gel) are prewashed with a buffer consisting of 0.5 ml 20 mM $NaH_2PO_4$/20 mM cystein-HCl/10 mM EDTA, pH 6.2, then added to purified 25–28 KD protein of Example 12.2 in the same buffer. The mixture is incubated for 16 hrs at 37° C. with rocking, then centrifuged and separated to stop the reaction. The supernatant contains pure 14–16 KD protein (as determined by SDS-PAGE, Example 11), which inhibits formation of rosettes of IgE-coated erythrocytes on U937 cells (Example 18 and Table VII).

14.3. By digestion with trypsin 0.05 ml of insolubilized trypsin (SIGMA, 86 BAEE units per ml) are equilibrated with phosphate buffer pH 8, then added to purified radiolabelled 25–28 KD protein (30'000 cpm) in phosphate buffer pH 8. Radiolabelled 25–28 KD is obtained by iodination with $^{125}I$ sodium iodide and chloramine T as described for a monoclonal antibody in Example 20. The digestion mixture is incubated for 16 hrs at 30° C. with rocking, then centrifuged to stop the reaction. The supernatant contains 14–16 KD protein, which is detected by autoradiography using XAR-5 X-ray film (Kodak).

Digestion with papain using radiolabelled 25–28 KD protein is performed likewise.

FIG. 4 shows the analysis result of a reversed phase HPLC on a Hi-Pore® RP-304 column using a gradient of 5 to 75% acetonitrile in 0.1% TFA of reaction products obtained on papain and trypsin digestion of the radiolabelled 25–28 KD protein of Example 11 (RPMI 8866) and Example 15 (colostrum), respectively. Counts per min (cpm) are given as a function of fraction number.

Example 15

Purification of IgE-BF from colostrum 15.1 Colostrum preparation

Colostrum is collected from 15 unselected healthy volunteers during the first two days of postpartum. Samples are treated with protease inhibitors (1 mM phenylmethylsulfonyl fluoride, 10 mM benzamidine, 50 mM ε-aminocaproic acid and 0.1% EDTA) and frozen immediately at −20° C. Five pools, made of 3 samples each, are processed in parallel. They are clarified by ultracentrifugation and then acidified (pH 4.0) with hydrochloric acid in order to precipitate the casein. The casein is removed, and the clear preparations are neutralized with 2M Tris and passed through a 0.45 μm filter. After filtration through Amicon XM50 membranes (molecular weight cut-off 50 KD) the samples are dialyzed against distilled water and lyophilized.

15.2 Pre-purification by gel chromatography 40 mg of lyophilized colostrum preparation (Example 15.1) are dissolved in 1.5 ml buffer (40 mM NaCl, 10 mM Tris-HCl, pH 8.0, containing 0.05% TWEEN 20™, polyoxyethylenesorbitan, 10 mM ε-aminocaproic acid and 0.1% BSA) and applied on a calibrated Sephadex® G-75 column (2.5×90 cm). Fractions corresponding to molecular weight comprised between 10–15, 15–20, 20–25, 25–30, 30–45 and 45–60 KD are pooled, concentrated to 1.5 ml and dialyzed against Hanks' balanced salt solution (HBSS). Fractions with polypeptides of molecular weight 25–30 KD contain the IgE-BF as shown in the IgE inhibition test of Example 18. When the protease inhibitors are omitted in step 15.1, active IgE-BF protein fragments appear in the fraction of 10–15 KD molecular weight.

15.3 Purification by immunoaffinity chromatography on Mab-94-Affigel

A colostrum preparation (Example 15.1) or a solution of pre-purified IgE-BF (Example 15.2) containing 10 mg protein per ml is filtered through a 2 ml column of Mab-94-Affigel (Example 10) at a flow rate of 5 ml/hr. The gel is washed successively with 20 volumes PBS supplemented with 0.5M NaCl and 0.05% Tween® 20, 5 volumes PBS and 5 volumes NaCl 0.9%. The protein content of the flow-through is monitored by on-line absorbance at 280 nm by means of a Uvicord® spectrophotometer to ensure complete removal of unbound proteins. The column is then eluted with 8 ml 0.1M glycine-HCl, pH 2.6, and the protein-containing fractions combined.

Although the IgE-BF obtained by this procedure shares many properties with IgE-BF from RPMI 8866 cell supernatant (Example 11), it differs with respect to binding to Mab-94 and Mab-135 as revealed in the radioimmunoassays described in Example 24.

15.4 Treatment with Mab-30-Affigel

Purified IgE-BF of Example 15.3 is processed on a column of Mab-30-Affigel (Example 10) exactly as described in Example 15.3.

The eluted protein of 25–28 RD is now indistinguishable from 25–28 KD protein obtained from RPMI 8866 cell supernatant (Example 12) in the following tests:

(1) Ion exchange HPLC on a TSK 545 DEAE column (LKB) using a gradient of 0 to 0.5M NaCl in 0.05M Tris-HCl, eluting at 0.17M NaCl.

(2) Reversed phase HPLC on a Hi-Pore®RP-304 column (Bio-Rad) using a gradient of 5 to 75% acetonitrile in 0.1% TFA, eluting at 31% acetonitrile.

(3) SDS polyacrylamide gel electrophoresis, wherein the proteins migrate with an approximate molecular weight of 25–28 KD.

(4) Identical pattern of peptide fragments observed on reversed phase HPLC on a Hi-Pore®RP-304 column using a gradient of 5 to 75% acetonitrile in 0.1% TFA of sample digested with papain or with trypsin (Example 14, FIG. 4).

(5) Inhibition of rosetting of U 937 cells by IgE-coated bovine erythrocytes using a 25–28 KD protein or a 14–16 KD protein obtained on papain digestion (Example 14).

(6) Identical immunoaffinity properties as revealed by the radioimmunoassays with Mab-94 or Mab-135 (Example 24).

Example 16

Cleavage of glycosidic linkages in the 25–28 KD protein

16.1. With N-glycanase

The 25–28 KD protein purified according to Example 15 (10 μl, 2.0 mg/ml) is boiled for 3 min in the presence of 0.5% SDS and. 0.1M β-mercaptoethanol. The sample is diluted to give a solution of 0.2M sodium phosphate buffer (pH 8.6), 5.0 mM EDTA and 1.25% NONIDET™P40, nonionic detergent, N-Glycanase (from *Flavobacterium meningosepticum*, Genzyme Corp., Boston, Mass.) is added to give a final concentration of 10 units/ml. The mixture is incubated overnight at 30° C. The reaction sample is analyzed by SDS polyacrylamide gel electrophoresis as described in Example 11. The resulting protein appears at slightly reduced apparent molecular weight of 24–26 KD.

16.2. With 0-glycosidase

Native 25–28 KD protein (20 μg) or radio-labelled 25–28 KD protein (30'000 cpm, Example 14.3) is incubated at 37° C. for 60 min in 50 μl of a mixture containing 0.001M calcium acetate, 10 mM D-galactonic acid γ-lactone, 0.02M Tris maleate buffer and 1 unit/ml neuraminidase (SIGMA). 2–4 milliunits of 0-glycosidase (from *Diplococcus pneumoniae*, Genzyme Corp.) are added and the incubation continued for 4 hrs. The reaction sample is analyzed by SDS-PAGE. The resulting protein again shows an apparent molecular weight of 24–26 KD.

Example 17

Blocking of IgE binding to monoclonal anti-IgE antibodies by purified IgE-BF Wells of polyvinyl chloride microtiter plates are incubated overnight with 200 μl of PBS containing 1 μg/ml of a monoclonal antibody (clone 175) specific to human IgE. Free binding capacity of the microtiter plate surface is blocked with PBS containing 10% FCS and 0.1% sodium azide. 150 μl of a PBS solution of purified IgE-BF of Example 11 of culture supernatant concentrated 100 fold from RPMI 8866 cells containing IgE-BF or of RPMI 8226 cells used as negative control are preincubated overnight at room temperature with 50 μl PBS containing $6\times10^4$ cpm $^{125}$I labelled IgE (specific activity $2.5\times10^4$ cpm/ng). 100 μl of this mixture is added to the anti-IgE antibody-coated wells; after 5 hrs incubation at room temperature the plates are washed and the radioactivity bound to the wells is measured in a Beckman gamma counter.

Cell supernatant from RPMI 8866 cells and purified IgE-BF of Example 11 inhibit the binding of radiolabelled IgE by 50 and 75%, respectively, as determined in relation to the negative control (RPMI 8226 cell supernatant) in several experiments.

The monoclonal antibody specific to human IgE is produced by a conventional procedure similar to that described in Example 1. Balb/c mice are immunized twice with 50 μg IgE PS in Complete Freund Adjuvant at 2 week intervals; three weeks after the last injection they receive an additional injection of 50 μg IgE PS in saline. Three days later spleen cells are fused with NSI/1-Ag4/1 myeloma cells. Clones are selected on the basis of RIAs employing IgE and IgG coated polyvinyl chloride microtiter plates and labelled goat anti-mouse IgG. The monoclonal antibody is specific to a determinant within the heat labile region of IgE.

Example 18

Inhibition by IGE-BF of the binding of IgE to RPMI 8866 or U 937 cells

Bovine erythrocytes are coated with a sub-optimal concentration of purified IgE PS (from Dr. K. Ishizaka, John Hopkins University, Baltimore, Md.). The coated erythrocytes are pre-incubated with either control buffer (HBSS-BSA) or test solutions for 60 min at 4° C. RPMI 8866 cells or U 937 cells are added. The preparation is centrifuged at 90×g and incubated at 4° C. for 2 hrs. The cells are examined under a fluorescence microscope after addition of acridine orange as described in Example 9.

Affinity chromatography experiments are performed as described in Example 11 or 15 employing purified IgE PS or polyclonal IgG coupled to Sepharose® 4B at 4 mg protein per ml gel. Effluents (filtrates) and eluates are concentrated to the initial volume of the sample and immediately neutralized and dialyzed against HBSS.

TABLE VII

Influence of IgE-BF on IgE PS binding to RPMI 8866 or U 937 cells

| Sample | % of cells forming rosette with E-IgE[a] | % rosette inhibition |
|---|---|---|
| Experiment No. 1: Colostrum processing | | |
| Controll buffer | 59 ± 2.8[b] | — |
| Colostrum preparation (10 μg/ml) | 28.3 ± 3.4 | 53 |
| IgE-Sepharose, eluate[c] | 41.3 ± 5.2 | 30 |
| IgG-Sepharose, eluate | 56.5 ± 3.1 | 4.5 |
| Mab-94-Affigel, effluent | 56 ± 5.4 | 5 |
| Mab-94-Affigel, eluate | 0 | 100 |
| Mab-94 (30 μg/ml) | 40.7 ± 3.9 | 31 |

TABLE VII-continued

Influence of IgE-BF on IgE PS binding to RPMI 8866 or U 937 cells

| Sample | | % of cells forming rosette with E-IgE[a] | % rosette inhibition |
|---|---|---|---|
| Experiment No. 2: Comparison of colostrum and RPMI 8866 IgE-BF after Mab-30-Affigel chromatography | | | |
| Control buffer | | 90.9 | — |
| Colostrum IgE-BF | 1/1[d] | 26.2 | 76 |
| | 1/2 | 76.7 | 20 |
| RPMI 8866 IgE-BF | 1/1 | 60.5 | 42 |
| Experiment No. 3: Comparison of colostrum IgE-BF after Mab-94-Affigel and after Mab-30-Affigel chromatography | | | |
| Control buffer | | 77.8 | — |
| Mab-94-Affigel, eluate | 1/2[d] | 19.2 | 77 |
| | 1/4 | 57.8 | 13 |
| | 1/8 | 81.8 | 0 |
| Mab-30-Affigel, eluate | 1/1 | 12.1 | 84 |
| Experiment No. 4: Comparison of colostrum IgE-BF after Mab-30-Affigel chromatography and after papain digestion (Example 14) | | | |
| Control buffer | | 91.8 | — |
| Colostrum IgE-BF | | 58.4 | 40 |
| Control buffer | | 88.9 | — |
| Papain digest | | 50.5 | 45 |

[a] E-IgE refers to bovine erythrocytes coated with IgE PS
[b] Mean ± 1 SD of 4 experiments
[c] The effluents and eluates are obtained as described in Example 15 and are used at a dilution of 1/10 after dialysis against HBSS
[d] dilution

Example 19

Preparation of a conjugate of F(ab')$_2$ fragment of Mab-135 with biotin

The purified F(ab')$_2$ fragment of Mab-135 (Example 6, 10 mg) is dialyzed at 1.0 mg/ml overnight against 1M NaHCO$_3$. The pH is checked and found to be between 8.2 and 8.6. Biotin succinimide ester (Biosearch) is dissolved in DMSO just before use at a concentration of 1.0 mg/ml.

0.6 ml of this solution are added to the antibody fragment solution, mixed immediately and left at room temperature for four hours. The reaction mixture is dialyzed against PBS containing 10 mmol sodium azide overnight, then stored in a refrigerator.

Example 20

Preparation of $^{125}$I labelled antibody Mab-135

40 μg Mab-135 are iodinated with 0.5 mCi $^{125}$I sodium iodide and chloramine T following the general procedure of F. C. Greenwood et al., Biochem. J. 89, 114 (1963). The reaction product is purified by chromatography on ion exchange resin Bio Rad Ag 1×8® and has a specific activity of 20,000 cpm/ng.

$^{125}$I labelled antibody Mab-176 and Mab-94 are prepared similarly.

Example 21

Radioimmunoassay for the detection of IgE-BF in cell supernatants and serum

Wells of polyvinyl chloride microtiter plates are incubated overnight at room temperature with 150 μl of 0.01M car-bonate buffer, pH 9, containing 15 μg/ml of Mab-176. The plates are then washed and reacted for 2 hrs at room temperature with 200 μl Hanks' balanced salt solution containing 10% fetal calf serum (HBSS-FCS), then again washed and incubated with 100 μl of test sample for 4 hrs at room temperature. The blank is determined by using HBSS-FCS. The plates are washed and incubated overnight at room temperature with $^{125}$I-Mab-135 (2 to 4×10$^5$ cpm in HBSS-FCS, Example 20), then washed and counted in a gamma counter. All the washings are performed with PBS (0.15M phosphate buffered saline, pH 7.2).

Culture supernatants derived from Fc$_e$R bearing cells containing IgE-BFs yield a significant binding of $^{125}$I-Mab-135 above background (0.5%). By contrast, culture supernatants containing no IgE-BFs give negative results (Table VIII). The presence or absence of IgE-BF in cell supernatants is confirmed by the rosette inhibition assay as described in Example 18. The RIA does not detect IgE-BFs from human colostrum, except after immunoaffinity chromatography over Mab-30 (Example 15.4).

TABLE VIII

Detection by RIA of the secretion of IgE-BFs by various human cell lines

| Cell lines [a] | cpm [b] | | Net cpm [c] |
|---|---|---|---|
| U266 | 410; | 420 | 266 |
| RPMI 8866 | 53,405; | 46,390 | 49,748 |
| EBV-CV$_4$ | 23,646; | 18,896 | 21,121 |
| EBV-HC | 23,495; | 30,724 | 26,949 |
| RPMI 8866-F7 | 25,769; | 25,565 | 25,517 |
| RPMI 8226 | 424; | 417 | 270 |

[a] The EBV transformed cell lines are obtained as described by M. Sarfati et al., Immunology 53, 207 (1984). The RPMI 8226 human B cell line is obtained from the American type tissue culture collection. Cell line U266 is from Dr. K. Nilssen, Uppsala, Sweden. RPMI 8866-F7 is a subclone of RPMI 8866 obtained by limiting dilution. The cell lines are cultured as described under Table II.
[b] Two replicates, unconcentrated cell supernatants.
[c] Mean, net value (Blank = 150).

Figure 5:
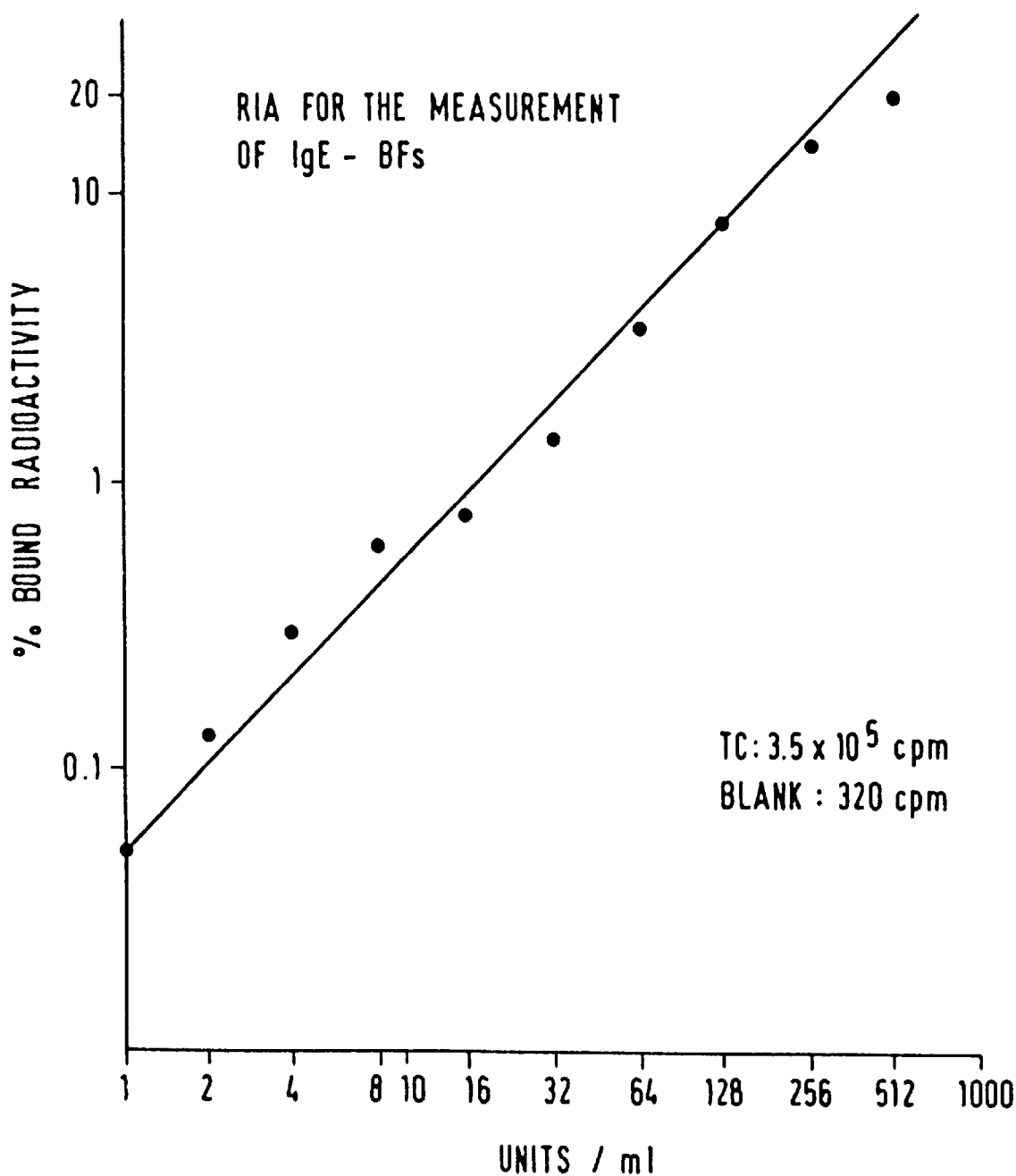
FIG. 5 shows a standard curve obtained by a serial two-fold dilution of a reference culture supernatant from RPMI 8866 cells containing IgE-BF as determined by the radioimmunoassay described in Example 21.

FIG. 5 shows a standard curve obtained by a serial two-fold dilution of a reference culture supernatant from RPMI 8866 cells containing IgE-BF. The sensitivity of the assay is such that it still detects. IgE-BFs at 1/50,000 dilution of the standard. The standard curve demonstrates a linear dependence of the radioactivity bound from the concentration of IgE-BF present in the tested solution in a concentration range of 1 to 1000.

Further proof for the specificity of the described RIA for IgE-BF as found in B cell supernatants comes from experiments wherein cell supernatants from RPMI 8866 cells known to contain IgE-BF are pretreated with IgE-Sepharose, IgG-Sepharose or ethanolamine-Sepharose, respectively. Whereas a clear reduction (between 57 and 80% in 4 different experiments) of bound radiolabelled Mab is observed in an RIA of IgE-Sepharose treated cell supernatant, no significant reduction is found with IgG-Sepharose or ethanolamine-Sepharose treated cell supernatant. The IgE-Sepharose bound IgE-BF can be recovered by elution with 0.1M glycine hydrochloride, pH 2.6, and detected by the RIA. The adsorption of IgE-BF on IgE-Sepharose is not complete due to the low affinity of IgE coupled to a solid carrier.

Example 22

Radioimmunoassay for the detection of IgE-BF in colostrum and serum

Wells of polyvinyl chloride microtiter plates are incubated overnight at room temperature with 100 μl of 0.01M carbonate buffer, pH 9, containing 15 μg/ml of Mab-94. The plates are then washed and reacted for 2 hrs at room temperature with 150 μl Hanks' balanced salt solution containing 10% fetal calf serum (HBSS-FCS), then again washed and incubated with 100 μl of test sample overnight at room temperature. The blank is determined by using HBSS-FCS. The plates are washed and incubated overnight at room temperature with 100 μl of $^{125}$I-Mab-94 in HBSS-FCS ($3\times10^5$ cpm per well, Example 20), then washed and counted in a gamma counter. All the washings are performed with PBS (0.15M phosphate buffered saline, pH 7.2).

Figure 6:
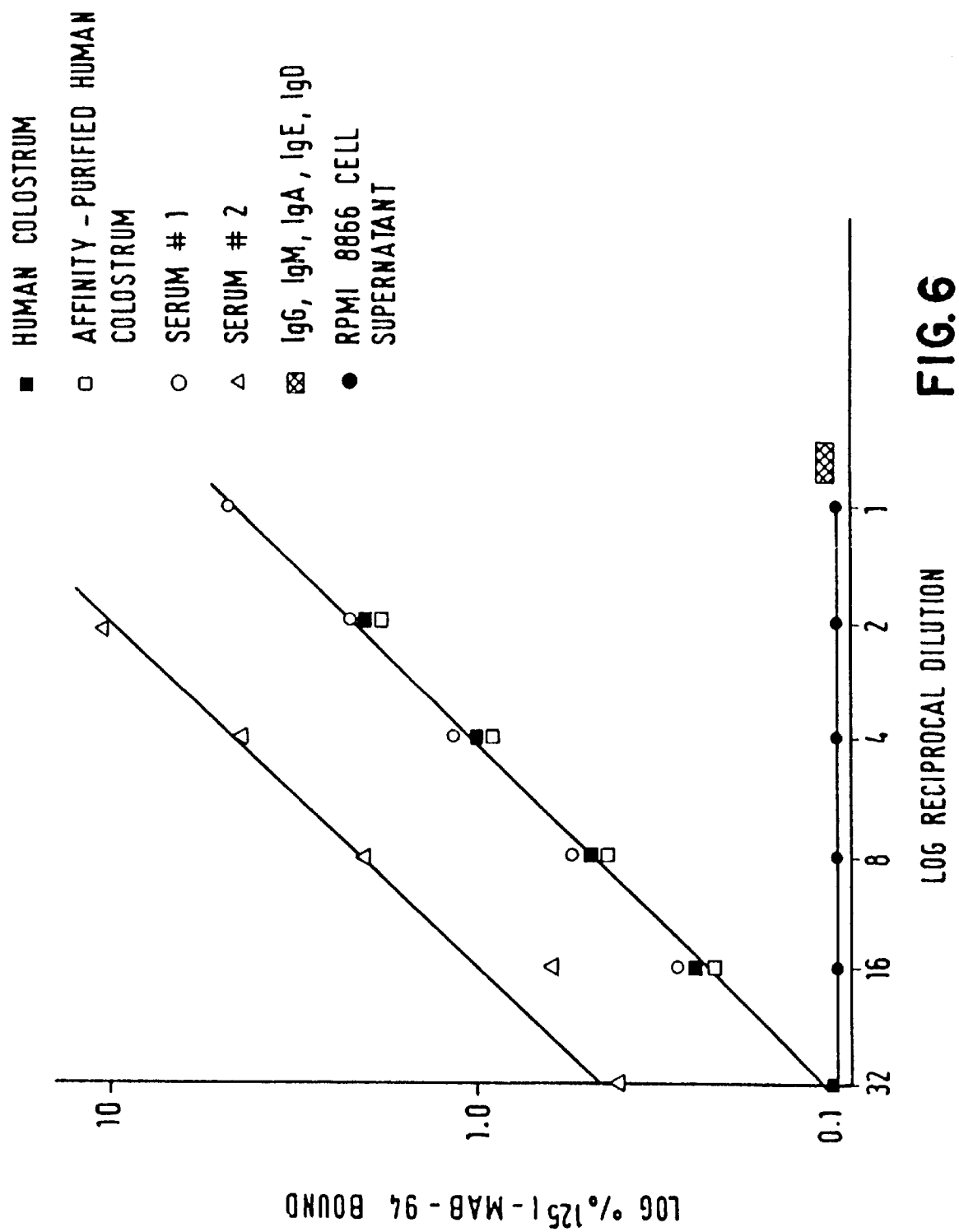
FIG. 6 shows curves obtained by a serial two-fold dilution of different samples as determined by the radioimmunoassay described in Example 22. The figure demonstrates the selectivity of the assay for IgE-BFs in colostrum and serum as compared to IgF-BF from B cell supernatant or to immunoglobulins of different classes.

FIG. 6 demonstrates that the RIA using Mab-94 and $^{125}$I-Mab-94 is useful for the detection of IgE-BF in colostrum and in serum giving a linear dependence for dilutions down to 1/32. The RIA is not influenced. by up to 100 μg/ml of other classes of immunoglobulins, i.e. IgG, IgM, IgA, IgE and IgD. Mab-94 does not detect IgE-BF as found in RPMI 8866 cell supernatant or IgE-BF from colostrum after immunoaffinity chromatography over Mab-30 (Example 15.4).

The selectivity of the described RIA is further demonstrated by the fact that the eluate from colostrum preparation adsorbed on IgE-Sepharose is readily detected, whereas a control eluate from colostrum preparation adsorbed on IgG-Sepharose does not react.

Example 23

Test kit for an RIA for IgE-BF

A test kit for the radioimmunoassay described in Example 21 or 22 contains:

Polyvinyl chloride microtiter plates 20 ml solution of Mab-176 or Mab-94 (10 μg/ml)

20 ml solution of $^{125}$I labelled Mab-135 or Mab-94 (specific activity $6\times10^6$ cpm/ml)

20 ml 0.02M carbonate buffer, pH 9

100 ml Hanks' balanced salt solution containing 10% FCS 200 ml PBS 2 ml reference cell supernatant of RPMI 8866 cells or colostrum preparation containing IgE-BF Standard curve.

Example 24

Selectivity of Mabs to IgE-BF from different sources and IGE-BF at different stage of processing Culture supernatant from RPMI 8866 cells is diluted 1:10 and found to bind 7.5% of $^{125}$I-Mab-135 in the RIA of Example 21, but 0% of $^{125}$I-Mab-94 in the RIA of Example 22. The sample is filtered through a column of Mab-135-Affigel (Example 10). The filtrate does not bind $^{125}$I-Mab-135 (0%), whereas the eluate (0.1M glycine-HCl, pH 2.6) binds 8.5% $^{125}$I-Mab-135. A sample of equal size is filtered through a column of Mab-94-Affigel. The filtrate binds 6.9% $^{125}$I-Mab-135, whereas the acid eluate contains no IgE-BF (0% binding). Throughout the experiment the filtrates and eluates are adjusted to the same volume to allow a comparison. The total count is approximately $3.5\times10^5$ cpm.

In the corresponding experiment, colostrum diluted 1:5 is found to bind 2.6% of $^{125}$I-Mab-94, but 0% of $^{125}$I-Mab-135. After adsorption on Mab-94-Affigel, 0% $^{125}$I-Mab-94 is bound in the filtrate versus 4.5% in the acid eluate. After adsorption on Affigel coupled to an unrelated Mab (e.g. a Mab to prolactin), 1.07% $^{125}$I-Mab-94 is bound in the filtrate versus 0% in the eluate.

However, when IgE-BF from colostrum purified on Mab-94-Affigel is adsorbed on Mab-30-Affigel (Example 15.4), the filtrate binds 0.2% $^{125}$I-Mab-135 and 0.6% $^{125}$I-Mab-94, and the eluate now 2.56% $^{125}$I-Mab-135, but 0% $^{125}$1-Mab-94. Another colostrum preparation, which is not purified on Mab-94-Affigel, gives 0% binding of $^{125}$I-Mab-135 and 5.75% binding of $^{125}$I-Mab-94. On absorption to Mab-30-Affigel, the filtrate binds 8% $^{125}$I-Mab-135 and 1.95% $^{125}$I-Mab-94, and the eluate 6.4% $^{125}$I-Mab-135 and 0.13% $^{12}$SI-Mab-94.

Example 25

Enzyme immunoassay (ELISA) for the detection of IGE-BF

Wells of polyvinyl chloride microtiter plates are coated with Mab-176 and blocked with HBSS-FCS as described in Example 21. The plates are incubated with 100 μl of test sample for 4 hrs at room temperature, then washed and incubated 4 hrs at room temperature with the Mab-135 fragment biotin conjugate (10 μg/ml) of Example 19. The plates are washed with PBS,then incubated overnight at room temperature with a 1/3000 dilution of an avidin-horseradish peroxidase conjugate (0.3 μg/ml) of Sigma. The amount of enzyme bound is determined by development (30 min at 37° C.) with a solution of 2,2'-azino-bis-(3-ethylbenzothiazoline-6-sulphonic acid) diammonium salt (ABTS, Boehringer Mannheim, 55 mg in 100 ml citrate/phosphate buffer 0.05M citrate/0.1M $Na_2HPO_4$, pH 4.0, containing 16 μl of 30% $H_2O_2$) and by photometric measurement at 405 nm.

Likewise, Mab-94 can be used to coat the plates and a Mab-94 biotin conjugate to detect IgE-BF from colostrum.

Example 26

Test kit for an ELISA of IgE-BF

A test kit for the ELISA described in Example 25 contains:

Polyvinyl chloride microtiter plates 20 ml solution of Mab-176 (10 μg/ml)

20 ml solution of Mab-135 fragment biotin conjugate (10 μg/ml)

20 ml 0.02M carbonate buffer, pH 9

100 ml Hank's balanced salt solution containing 10% FCS 1 mg lyophilized avidin-horseradish peroxidase conjugate 11 mg ABTS 20 ml citrate/phosphate buffer 0.05M citrate/0.1M $Na_2HPO_4$ 1 ml 30% $H_2O_2$ 200 ml PBS 2 ml reference solution containing IgE-BF.

Example 27

Pharmaceutical preparations (parenteral administration)

100 mg of IgE-BF purified by affinity chromatography (Example 11 or 15) are dissolved in 600 ml of 5N human serum albumin. The resulting solution is passed through a bacteriological filter and the filtered solution is subdivided under aseptic conditions into 100 vials each containing 1 mg of active compound. The vials which are suitable for parenteral administration are preferably stored in the cold, for example at −20° C.

In the same manner, vials containing 1 mg of the 25–28 KD protein (Example 11 or Example 15) may be prepared by using 100 mg of lyophilized 25–28 KD protein.

I claim:

1. A process for the preparation of an individual protein or a fragment of the individual protein, the individual protein or the fragment of the individual protein possessing immunoglobulin E binding and immunoglobulin E synthesis suppressing activity, comprising the steps of:

obtaining a culture supernatant of a continuous human B-cell line, said continuous human B-cell line capable of expressing immunoglobulin E binding factors and receptors for immunoglobulin E;

contacting a solution from said continuous human B-cell line culture supernatant containing said immunoglobulin E binding factors with a carrier material bearing monoclonal antibodies which bind to said immunoglobulin E binding factors, said monoclonal antibodies being secreted by any of the hybridoma cell lines 207.25 A.4.4/30, 207.25 A4.4/45 or 208.25 D.2/94;

allowing said immunoglobulin E binding factors to bind to said monoclonal antibodies on said carrier material;

removing unbound proteins and other foreign substances;

selectively splitting off said immunoglobulin E binding factors from said monoclonal antibodies on said carrier material;

purifying by isolation said immunoglobulin E binding factors: and separating said purified immunoglobulin E binding factors to obtain individual optionally glycosylated proteins and fragments thereof;

wherein the individual protein;

(a) is a constituent of a substantially pure human immunoglobulin E binding factor, (b) possesses immunoglobulin E binding and immunoglobulin E synthesis suppressing activity, (c) is homogeneous as determined by SDS-PAGE analysis, (d) has an apparent molecular weight of 25–28 kD as determined by SDS-PAGE analysis, and (e) is optionally glycosylated, and wherein the fragment of the individual protein;

(f) is a constituent of a substantially pure human immunoglobulin E binding factor, (g) possesses immunoglobulin E binding and immunoglobulin E synthesis suppressing activity, (h) is homogeneous as determined by SDS-PAGE analysis, (i) has an apparent molecular weight of 10–20 kD as determined by SDS-PAGE analysis, and (j) is obtainable by partial enzymatic digestion of said substantially pure immunoglobulin E binding factor.

2. A process according to claim 1 wherein the solution containing IgE-BF is a culture supernatant of the cell line RPMI 8866.

3. A process according to claim 1 wherein the purified IgE-BF is further purified by ion exchange chromatography.

4. A process according to claim 1 wherein the purified IgE-BF is further purified by preparative reversed phase HPLC.

5. A process according to claim 1 wherein the purified IgE-BF is separated into its individual optionally glycosylated proteins by sodium dodecyl sulphate polyacrylamide gel electrophoresis (SDS-PAGE).

6. A process according to claim 1 wherein the purified IgE-BF or individual glycosylated proteins are treated with enzymes cleaving glycosidic linkages.

7. A process according to claim 1 wherein the purified IgE-BF or individual optionally glycosylated proteins are treated with a protease.

8. A process according to claim 7 wherein the protease is papain or trypsin.

* * * * *